US010258616B2

(12) United States Patent
Danagher et al.

(10) Patent No.: US 10,258,616 B2
(45) Date of Patent: *Apr. 16, 2019

(54) HYDROMORPHONE AND NALOXONE FOR TREATMENT OF PAIN AND OPIOID BOWEL DYSFUNCTION SYNDROME

(71) Applicant: Euro-Celtique S.A., Luxembourg (LU)

(72) Inventors: Helen Kathleen Danagher, Cambridge (GB); Hassan Mohammad, Cambridge (GB); Malcolm Walden, Cambridge (GB); Geoffrey Gerard Hayes, Cambridge (GB); Jonathon Oliver Whitehouse, Cambridge (GB); Thinnayam Naganathan Krishnamurthy, Scarborough (CA); Ricardo Alberto Vargas Rincon, Mississauga (CA)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,829

(22) Filed: Nov. 10, 2017

(65) Prior Publication Data

US 2018/0064705 A1 Mar. 8, 2018

Related U.S. Application Data

(63) Continuation of application No. 15/036,735, filed as application No. PCT/EP2014/074537 on Nov. 13, 2014, now Pat. No. 9,814,710.

(30) Foreign Application Priority Data

Nov. 13, 2013 (EP) ..................................... 13192793

(51) Int. Cl.
*A61K 31/44* (2006.01)
*A61K 31/485* (2006.01)
*A61K 9/00* (2006.01)
*A61K 9/48* (2006.01)

(52) U.S. Cl.
CPC .......... *A61K 31/485* (2013.01); *A61K 9/0053* (2013.01); *A61K 9/48* (2013.01)

(58) Field of Classification Search
CPC .................................................. A61K 31/485
USPC ...................................................... 514/282
See application file for complete search history.

(56) References Cited

U.S. PATENT DOCUMENTS

| | | | |
|---|---|---|---|
| 3,965,256 A | 6/1976 | Leslie | |
| 4,366,310 A | 12/1982 | Leslie | |
| 4,457,933 A | 7/1984 | Gordon et al. | |
| 4,647,599 A | 3/1987 | Bezzegh et al. | |
| 4,705,695 A | 11/1987 | Lehmann et al. | |
| 4,769,372 A | 9/1988 | Kreek et al. | |
| 4,785,000 A | 11/1988 | Kreek et al. | |
| 4,987,136 A | 1/1991 | Kreek et al. | |
| 5,004,613 A | 4/1991 | Radebaugh et al. | |
| 5,958,452 A | 9/1999 | Oshlack et al. | |
| 6,153,644 A | 11/2000 | Owens et al. | |
| 6,277,384 B1 | 8/2001 | Kaiko et al. | |
| 6,375,957 B1 | 4/2002 | Kaiko et al. | |
| 6,419,959 B1 | 7/2002 | Walter et al. | |
| 6,475,494 B2 | 11/2002 | Kaiko et al. | |
| 6,488,961 B1 | 12/2002 | Robinson et al. | |
| 6,696,066 B2 | 2/2004 | Kaiko et al. | |
| 6,716,449 B2 | 4/2004 | Oshlack et al. | |
| 7,172,767 B2 | 2/2007 | Kaiko et al. | |
| 7,419,686 B2 | 9/2008 | Kaiko et al. | |
| 7,749,542 B2 | 7/2010 | Kaiko et al. | |
| 8,105,631 B2 | 1/2012 | Kaiko et al. | |
| 8,114,383 B2 | 2/2012 | Bartholomäus et al. | |
| 8,597,681 B2 | 12/2013 | Park et al. | |
| 8,673,355 B2 | 3/2014 | Kaiko et al. | |
| 8,822,487 B2 | 9/2014 | Kaiko et al. | |
| 8,846,090 B2 | 9/2014 | Brogmann et al. | |
| 8,846,091 B2 | 9/2014 | Brogmann et al. | |
| 8,932,630 B1 | 1/2015 | Kaiko et al. | |
| 8,936,808 B1 | 1/2015 | Kaiko et al. | |
| 8,969,369 B2 | 3/2015 | Caruso et al. | |
| 9,056,051 B2 | 6/2015 | Caruso et al. | |
| 9,084,729 B2 | 7/2015 | Caruso et al. | |
| 9,161,252 B2 | 10/2015 | Caruso et al. | |
| 9,161,937 B2 | 10/2015 | Caruso et al. | |
| 9,168,252 B2 | 10/2015 | Caruso et al. | |
| 9,205,082 B2 | 12/2015 | Kaiko et al. | |

(Continued)

FOREIGN PATENT DOCUMENTS

| | | |
|---|---|---|
| CA | 2766172 | 1/2001 |
| CA | 2478558 | 9/2003 |

(Continued)

OTHER PUBLICATIONS

Abbaspour et al, "Thermal treating as a tool to produce plastic pellets based on Eudragit RS PO and RL PO aimed for tabletting", European Journal of Pharmaceutics and Biopharmaceutics 2007, 67, pp. 260-267.

Alvarez, "Sustained Release—Comparison of Acrylic & Cellulose-Based Matrix Formers for Sustained Drug Release", Drug Delivery Technology 2006, vol. 6., No. 3.

Azamari et al., "Thermal treating as a tool for sustained release of indomethacin from Eudragit RS and RL matrices," International Journal of Pharmaceutics, 246, 171-177 (2002).

Azarmi et al, "Mechanistic evaluation of the effect of thermal-treating on Eudragit RS matrices", Il farmaco 2005, 50, pp. 925-930.

Bell et al., "The prevalence, severity, and impact of opioid-induced bowel dysfunction: results of a US and European Patient Survey (PROBE 1)," Pain Medicine, 10(1):35-42 (2009).

(Continued)

*Primary Examiner* — Raymond J Henley, III
(74) *Attorney, Agent, or Firm* — Alan L. Koller; Weiying Yang

(57) ABSTRACT

The present invention relates to prolonged release pharmaceutical dosage forms comprising hydromorphone or a pharmaceutically acceptable salt thereof and naloxone or a pharmaceutically acceptable salt thereof for use in the treatment of pain.

18 Claims, 2 Drawing Sheets

(56) References Cited

U.S. PATENT DOCUMENTS

| | | | |
|---|---|---|---|
| 9,283,216 | B2 | 3/2016 | Caruso et al. |
| 9,283,221 | B2 | 3/2016 | Caruso et al. |
| 9,345,701 | B1 | 5/2016 | Caruso et al. |
| 9,358,230 | B1 | 6/2016 | Caruso et al. |
| 9,474,750 | B2 | 10/2016 | Kaiko et al. |
| 9,480,685 | B2 | 11/2016 | Caruso et al. |
| 9,511,066 | B2 | 12/2016 | Caruso et al. |
| 9,555,000 | B2 | 1/2017 | Brogmann et al. |
| 9,655,855 | B2 | 5/2017 | Brogmann et al. |
| 9,700,508 | B2 | 7/2017 | Danagher et al. |
| 9,814,710 | B2 * | 11/2017 | Danagher ............ A61K 31/485 |
| 9,901,540 | B2 | 2/2018 | Danagher et al. |
| 2002/0040139 | A1 | 4/2002 | Billotte et al. |
| 2003/0004177 | A1 | 1/2003 | Kao et al. |
| 2003/0229111 | A1 | 12/2003 | Oshlack et al. |
| 2004/0081694 | A1 | 4/2004 | Oshlack et al. |
| 2004/0176402 | A1 | 9/2004 | Oshlack et al. |
| 2004/0242617 | A1 | 12/2004 | Christoph |
| 2005/0025802 | A1 | 2/2005 | Richard et al. |
| 2005/0032546 | A1 | 2/2005 | Kehr |
| 2005/0074493 | A1 | 4/2005 | Mehta et al. |
| 2005/0079221 | A1 | 4/2005 | Groenewoud |
| 2005/0095291 | A1 | 5/2005 | Oshlack et al. |
| 2005/0232987 | A1 | 10/2005 | Srinivasan |
| 2005/0245483 | A1 | 11/2005 | Brogmann et al. |
| 2005/0245556 | A1 | 11/2005 | Brogmann et al. |
| 2006/0039970 | A1 | 2/2006 | Oshlack et al. |
| 2006/0270611 | A1 | 11/2006 | Dries et al. |
| 2007/0014732 | A1 | 1/2007 | Sackler |
| 2007/0026025 | A1 | 2/2007 | Mitchell |
| 2007/0048364 | A1 | 3/2007 | Peng et al. |
| 2007/0141147 | A1 | 6/2007 | Heil et al. |
| 2007/0259045 | A1 | 11/2007 | Mannion et al. |
| 2007/0298103 | A1 | 12/2007 | Hayes |
| 2008/0069875 | A1 | 3/2008 | Kakiguchi et al. |
| 2008/0145429 | A1 | 6/2008 | Leyendecker et al. |
| 2008/0280921 | A1 | 11/2008 | Dreyer et al. |
| 2009/0214640 | A1 | 8/2009 | Szabo et al. |
| 2010/0151011 | A1 | 6/2010 | Benke |
| 2010/0183687 | A1 | 7/2010 | Cox et al. |
| 2010/0210843 | A1 | 8/2010 | Hudson et al. |
| 2010/0226943 | A1 | 9/2010 | Brennan et al. |
| 2010/0227876 | A1 | 9/2010 | Rech |
| 2010/0331354 | A1 | 12/2010 | Wermeling |
| 2011/0020451 | A1 | 1/2011 | Bartholomäus et al. |
| 2011/0077222 | A1 | 3/2011 | Schaefer et al. |
| 2011/0077238 | A1 | 3/2011 | Leech et al. |
| 2011/0172259 | A1 | 7/2011 | Leyendecker et al. |
| 2011/0287095 | A1 | 11/2011 | Park et al. |
| 2012/0108621 | A1 | 5/2012 | Brogmann et al. |
| 2012/0135075 | A1 | 5/2012 | Mohammad |
| 2012/0183612 | A1 | 7/2012 | Brogmann et al. |
| 2012/0225901 | A1 | 9/2012 | Leyendecker et al. |
| 2013/0090349 | A1 | 4/2013 | Geisler et al. |
| 2013/0165467 | A1 | 6/2013 | Hayes et al. |
| 2013/0178492 | A1 | 7/2013 | Danagher et al. |
| 2013/0197021 | A1 | 8/2013 | Mohammad et al. |
| 2013/0245054 | A1 | 9/2013 | Prater et al. |
| 2013/0330409 | A1 | 12/2013 | Mohammad |
| 2014/0031382 | A1 | 1/2014 | Leyendecker et al. |
| 2015/0283091 | A1 | 10/2015 | Vargas Rincon et al. |
| 2016/0095853 | A1 | 4/2016 | Prater et al. |
| 2016/0296516 | A1 | 10/2016 | Danagher et al. |

FOREIGN PATENT DOCUMENTS

| | | |
|---|---|---|
| CA | 2764517 | 12/2010 |
| CA | 2739751 | 11/2011 |
| CA | 2798885 | 11/2011 |
| CA | 2822553 | 6/2012 |
| CA | 2795324 | 5/2014 |
| DE | 4325465 | 2/1995 |
| DE | 10215131 | 10/2003 |
| EC | SP1998-2720 | 10/1998 |
| EC | SP2000-3314 | 1/2000 |
| EC | SP2010-10416 | 8/2010 |
| EP | 0425154 A1 | 5/1991 |
| EP | 0441245 | 8/1991 |
| EP | 0714661 A1 | 6/1996 |
| EP | 0880352 | 12/1998 |
| EP | 0913152 | 5/1999 |
| EP | 1557179 A1 | 7/2005 |
| EP | 1695700 | 8/2006 |
| EP | 1813276 A1 | 8/2007 |
| EP | 1961421 A1 | 8/2008 |
| EP | 2255808 | 5/2011 |
| EP | 3068397 | 9/2016 |
| FR | 2946533 | 12/2010 |
| GB | 2418854 A | 4/2006 |
| GB | 2447898 A | 10/2008 |
| JP | 2006265184 | 10/2006 |
| WO | WO199614058 | 5/1996 |
| WO | WO1997016172 | 5/1997 |
| WO | WO1998035679 | 8/1998 |
| WO | WO199901111 | 1/1999 |
| WO | WO199932119 | 7/1999 |
| WO | WO2001032180 | 5/2001 |
| WO | WO200154683 | 8/2001 |
| WO | WO200158447 | 8/2001 |
| WO | WO2002060385 | 8/2002 |
| WO | WO2002092060 | 11/2002 |
| WO | WO20020100382 | 12/2002 |
| WO | WO2003013479 | 2/2003 |
| WO | WO2003013525 | 2/2003 |
| WO | WO2003018588 | 3/2003 |
| WO | WO2003024444 | 3/2003 |
| WO | WO2003084504 | 10/2003 |
| WO | WO2003084520 | 10/2003 |
| WO | WO2004004683 | 1/2004 |
| WO | WO2004091622 | 10/2004 |
| WO | WO2004091623 | 10/2004 |
| WO | WO2004091665 | 10/2004 |
| WO | WO2004098567 | 11/2004 |
| WO | WO2005077957 | 8/2005 |
| WO | WO2005079760 | 9/2005 |
| WO | WO2005097801 | 10/2005 |
| WO | WO2005117873 | 12/2005 |
| WO | WO2006038226 | 4/2006 |
| WO | WO2006043025 | 4/2006 |
| WO | WO2006078842 | 7/2006 |
| WO | WO2006079550 | 8/2006 |
| WO | WO2006092064 | 9/2006 |
| WO | WO2006133941 | 12/2006 |
| WO | WO2007013047 | 2/2007 |
| WO | WO2007039122 | 4/2007 |
| WO | WO2007068615 | 6/2007 |
| WO | WO2008023261 | 2/2008 |
| WO | WO2008049657 | 5/2008 |
| WO | WO2010003963 | 1/2010 |
| WO | WO2010032073 | 3/2010 |
| WO | WO2010032128 | 3/2010 |
| WO | WO2010033195 | 3/2010 |
| WO | WO2010034342 | 4/2010 |
| WO | WO2010034344 | 4/2010 |
| WO | WO2010068789 | 6/2010 |
| WO | WO2010078486 | 7/2010 |
| WO | WO2010081034 | 7/2010 |
| WO | WO2010088911 | 8/2010 |
| WO | WO2010096045 | 8/2010 |
| WO | WO2010096788 | 8/2010 |
| WO | WO2010096790 | 8/2010 |
| WO | WO2010103039 | 9/2010 |
| WO | WO2010105672 | 9/2010 |
| WO | WO2010105673 | 9/2010 |
| WO | WO2010112942 | 10/2010 |
| WO | WO2010120232 | 10/2010 |
| WO | WO2010121619 | 10/2010 |
| WO | WO2010123999 | 10/2010 |
| WO | WO2010140007 | 12/2010 |
| WO | WO2010141505 | 12/2010 |
| WO | WO2010142814 | 12/2010 |
| WO | WO2010144641 | 12/2010 |
| WO | WO2011009020 | 1/2011 |
| WO | WO2011009602 | 1/2011 |

(56) References Cited

FOREIGN PATENT DOCUMENTS

| WO | WO2011009603 | 1/2011 |
|---|---|---|
| WO | WO2011009604 | 1/2011 |
| WO | WO2011021029 | 2/2011 |
| WO | WO2011031350 | 3/2011 |
| WO | WO2011141488 | 11/2011 |
| WO | WO2011141489 | 11/2011 |
| WO | WO2011141490 | 11/2011 |
| WO | WO2012076907 | 6/2012 |
| WO | WO2012089738 | 7/2012 |
| WO | WO2013050539 | 4/2013 |
| WO | WO2014071499 | 5/2014 |
| WO | WO2015071380 | 5/2015 |

OTHER PUBLICATIONS

Billa et al, "Diclofenac Release from Eudragit-Containing Matrices and Effects of Thermal Treatment", Drug Development and Industrial Pharmacy 1998, 24, pp. 45-50.
Cameron et al, "Controlled-Release Theophylline Tablet Formulations containing Acrylic Resins, II. Combination Resin Formulations", Drug Development and Industrial Pharmacy 1987, 13, pp. 1409-1427.
Clemens et al, "Bowel function during pain therapy with oxycodone/naloxone prolonged release tablets in patients with advanced cancer", International Journal of Clinical Practice 2011, 65, pp. 472-478.
Clinical Trials Study No. NCT00992576, "Optimisation of Hydromorphone—Naloxone Ratio for the Treatment of Pain," ClinicalTrials.gov (2009).
Coleman, "Reducing the abuse potential of controlled substances", Pharmaceutical Medicine 2010, 24, pp. 24-36.
Culpepper-Morgan et al., "Treatment of opioid-induced constipation with oral naloxone: A pilot study." Clinical Trials and Therapeutics, (1992) vol. 52(1): 90-95.
Davis et al, "Recent development in therapeutics for breakthrough pain", Expert Review of Neuropathics 2010, 10, pp. 757-773.
Draganoiu et al, "Development and in vitro / in vivo Evaluation of Extended Release Propranolol Tablets", Pharm. Ind. 2006, 68, pp. 111-115.
Dumicic et al, "The effect of water on matrix formation in sustained release tablets containing poly(ethyl acrylate, methyl methacrylate)", J. Drug Del. Sci. Tech. 2005, 15, pp. 389-395.
English Translation of EP 0880352 provided by Google Patents, Accessed on Apr. 1, 2017.
European Pharmacopoeia, 4th Edition, Directorate for the Quality of Medicines of the Council of Europe, Council of Europe Strasbourg, 2001, ISBN:92-871-4587-3, p. 535.
Goforth et al, "Hydromorphone-OROS formulation", Expert Opinion on Pharmacotherapy 2010, 11, pp. 1207-1214.
Haririan et al, "Formulation of Controlled Release Matrix Tables of Isosorbide Dinitrate", Indian Journal of Pharmaceutical Sciences 2001, 63, pp. 24-29.
Hawkes et al., "Effect of enteric-release formulation of naloxone on intestinal transit in volunteers taking codeine"; Aliment Pharm Ther (2001) vol. 15, pp. 625-630.
Holzer, "New Approaches to the Treatment of Opioid-Induced Constipation," Eur. Rev. Med. Pharmacol. Sci., 12 Suppl 1:119-27 (2008).
I. Jurna and J. Baldauf, "Oral administration of slow-release naloxone for prevention of constipation but not analgesia following oral morphine," Der Schmerz, 7, 314-321 (1993) and translation thereof. Index Merck 14th, Merck & Co., USA, 2006, No. 0006362, 0004803.
International Search Report and Written Opinion corresponding to International Application No. PCT/EP2014/074537 dated Feb. 10, 2015.
International Application No. PCT/CA2015/000206: International Search Report dated Jul. 27, 2015.
International Application No. PCT/EP2011/057566, International Search Report dated Feb. 3, 2012.
International Application No. PCT/EP2011/057567: International Search Report dated Aug. 9, 2011.
International Application No. PCT/EP2011/057568: International Search Report dated Aug. 17, 2011.
International Application No. PCT/GB2010/050948: International Preliminary Report on Patentability and Written Opinion, The International Bureau of WIPO, Geneva, Switzerland, dated Dec. 15, 2011.
International Application No. PCT/GB2010/050948: International Search Report, European Patent Office, Netherlands, dated Dec. 1, 2011.
International Search report and Written Opinion corresponding to International Patent Application No. PCT/CA2013/000932 dated Mar. 13, 2014.
Jenquin et al, "Relationship of Film Properties to Drug Release from Monolithic Films Containing Adjuvants", Journal of Pharmaceutical Science 1992, 81, pp. 983-989.
Jost, "Management of cancer pain: ESMO Clinical Practice Guidelines", Annals of Oncology 2010, 21, pp. v257-v260.
Kalso et al., "Opioids in Chronic Non-Cancer Pain: Systematic Review of Efficacy and Safety," Pain, 112, 372-380 (2004).
Kao et al, "The Influence of Eudragit S-100 on the Release of Chlopheniramine Maleate from Matrix Tablets Containing Eudragit RS-PM", The Chinese Pharmaceutical Journal 1994, 46, 257-267.
Krajacic et al, "Matrix formation in sustained release tablets: possible mechanism of dose dumping", International Journal of Pharmaceutics 2003, 251, pp. 67-78.
Latasch et al., "Aufhebun einer Morphin-induzierten Obstipation durch orales Naloxon," with translation ("Oral Naloxone Antagonizes Morphine-Induced Constipation"), Anaesthesist, 46, 191-194 (1997).
Leppert, "Dihydrocodeine as an opioid analgesic for the treatment of moderate to severe chronic pain", Current Drug Metabolism 2010, 11, pp. 494-506.
Leppert, "Role of oxycodone/naloxone in cancer pain management", Pharmacological Reports 2010, 62, 578-591.
Liu et al., "Low-dose Oral Naloxone Reverses Opioid-Induced Constipation and Analgesia," J. Pain Symptom Manage, 23(1):48-53 (2002).
Mansour et al, "Materials for Pharmaceutical Dosage Forms: Molecular Pharmaceutics and Controlled Release Drug Delivery Aspects," Int. J. Mol. Sci. 2010, 11, 3298-3322.
Meissner et al., "A randomized controlled trial with prolonged-release oral oxycodone and naloxone to prevent and reverse opioid-induced constipation," Eur. J. Pain, vol. 13, pp. 56-64 (2009).
Meissner et al., "Oral naloxone reverses opioid-associated constipation", Pain, vol. 84, pp. 105-109 (2000).
Nagata, "Advantages to HPMC Capsules: A New Generation's", Drug Development and Delivery, vol. 2, No. 2, Mar./Apr. 2002, pp. 1-8.
Oliveto et al., "Hydromorphone-naloxone combinations in opioid-dependent humans under a naloxone novel-response discrimination procedure," Exp. and Clin. Psychopharmacology, vol. 6, No. 2, 169-178 (1998).
Oxycodone / Naloxone Combination Tablet Reduces Opioid-induced Bowel Dysfunction in Patients with Chronic Severe Pain, , XP00263606, [Online], Sep. 27, 2007 [retrieved on May 5, 2011] Retrieved from the internet: <URL: http://www.medicalnewstoday.com/printerfriendlynews.php?newsid=83795 >, pp. 1-2.
Palladone® retard 4, 8, 16, 24 mg, Product Label (2011).
Pappagallo, M., "Incidence, prevalence, and management of opioid bowel dysfunction," Am. J. Surg. (2001) 182 suppl. 11S-18S.
Portenoy, "Constipation in the Cancer Patient: Causes and Management Treatment of Constipation" Cancer Pain, 71(2):303-311 (1987).
Rentz et al., "Validation of the Bowel Function Index to Detect Clinically Meaningful Changes in Opioid-Induced Constipation," Journal of Medical Economics (JME), 12(0):371-383 (2009).
Sadeghi et al, "Tableting of Eudragit RS and Propranolol Hydrochloride Solid Dispersion: Effect of Particle Size, Compaction

(56) References Cited

OTHER PUBLICATIONS

Force, and Plasticizer Addition on Drug Release", Drug Development and Industrial Pharmacy 2004, 30, pp. 759-766.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Taiwan Application No. 100116427: Office Action and Search Report dated Mar. 12, 2013.
Vela et al, "Effect of Acrylic Resins on the Rheological and Compressibility Properties of Paracetamol: Formulation of directly compressible Matrix Systems", Il farmaco 1995, 50, pp. 201-215.
Woods et al, "Opioid abuse and dependence: Treatment review and future options", Formulary 2010, 45, pp. 284-291.
Wurster et al, "Effect of Curing on Water Diffusivities in Acrylate Free Films as Measured via Sorption Technique", AAPS PharmSciTech 2007, 8, pp. E1-E6.
Yasser et al, "Effect of Eudragit® RS 30D andTalc Powder on Verapamil Hydrochloride Release from Beads Coated with Drug Layered Matrices", AMPS PharmSciTech 2007, 9, pp. 75-83.

\* cited by examiner

HYDROMORPHONE AND NALOXONE FOR TREATMENT OF PAIN AND OPIOID BOWEL DYSFUNCTION SYNDROME

CROSS-REFERENCE TO RELATED APPLICATIONS

This application is a continuation of application No. U.S. Ser. No. 15/036,735, filed May 13, 2016, now U.S. Pat. No. 9,814,710, which is the National Phase under 35 U.S.C. § 371 of PCT/EP2014/074537, filed Nov. 13, 2014, which claims priority to European Patent Application No. EP13192793.1, filed Nov. 13, 2013; each of which is hereby incorporated by reference.

TECHNICAL FIELD OF THE INVENTION

The present invention relates to prolonged release pharmaceutical dosage forms comprising hydromorphone or a pharmaceutically acceptable salt thereof and naloxone or a pharmaceutically acceptable salt thereof for use in the treatment of pain.

BACKGROUND OF THE INVENTION

According to the pain ladder model of the World Health Organization opioids are indicated for the treatment of moderate to severe pain. Opioids for pain treatment are commonly administered as prolonged release pharmaceutical compositions, which are taken continuously e.g. on a 12 hour regimen.

However, opioid treatment can elicit side effects of which the most troublesome include opioid bowel syndrome and in particular opioid-induced constipation. It has been reported that up to a third of patients reduce or discontinue opioid treatment as a consequence of problems with constipation (Bell et al., Pain Med 2009, 10, 35-42).

There is thus a continuing need for efficient pain treatment with opioids. There is also need for formulations that do not exhibit a food effect, which is one of the problems that the present invention seeks to solve.

SUMMARY OF THE INVENTION

It is an objective of the present invention to provide prolonged release pharmaceutical dosage forms comprising opioids for treatment of pain which improve side effects, in particular opioid-induced constipation.

It is also an objective to provide prolonged release pharmaceutical dosage forms comprising opioids for treatment of pain which improve side effects, in particular opioid-induced constipation, and optionally which exhibit reduced or no food effect.

These and other objectives as they will become apparent from the ensuing description are attained by the subject matter of the independent claims. Some of the preferred embodiments are referred to by the dependent claims.

To some extent, the present invention is based on findings which are described in the examples. These findings suggest that prolonged release formulations of specific combinations of hydromorphone or a pharmaceutically acceptable salt thereof and naloxone or a pharmaceutically acceptable salt thereof can be used to efficiently treat pain and reduce or prevent opioid-induced constipation without substantial loss of therapeutically effective levels of analgesia. These specific combinations, in some embodiments, include hydromorphone HCl and naloxone HCl in a weight ratio of hydromorphone HCl:naloxone HCl ranging from about 1:1 to about 1:2. The weight ratio of hydromorphone HCl:naloxone HCl may be about 1:1, about 1:1.5, or about 1:2.

DETAILED DESCRIPTION OF THE INVENTION

Figure 1:
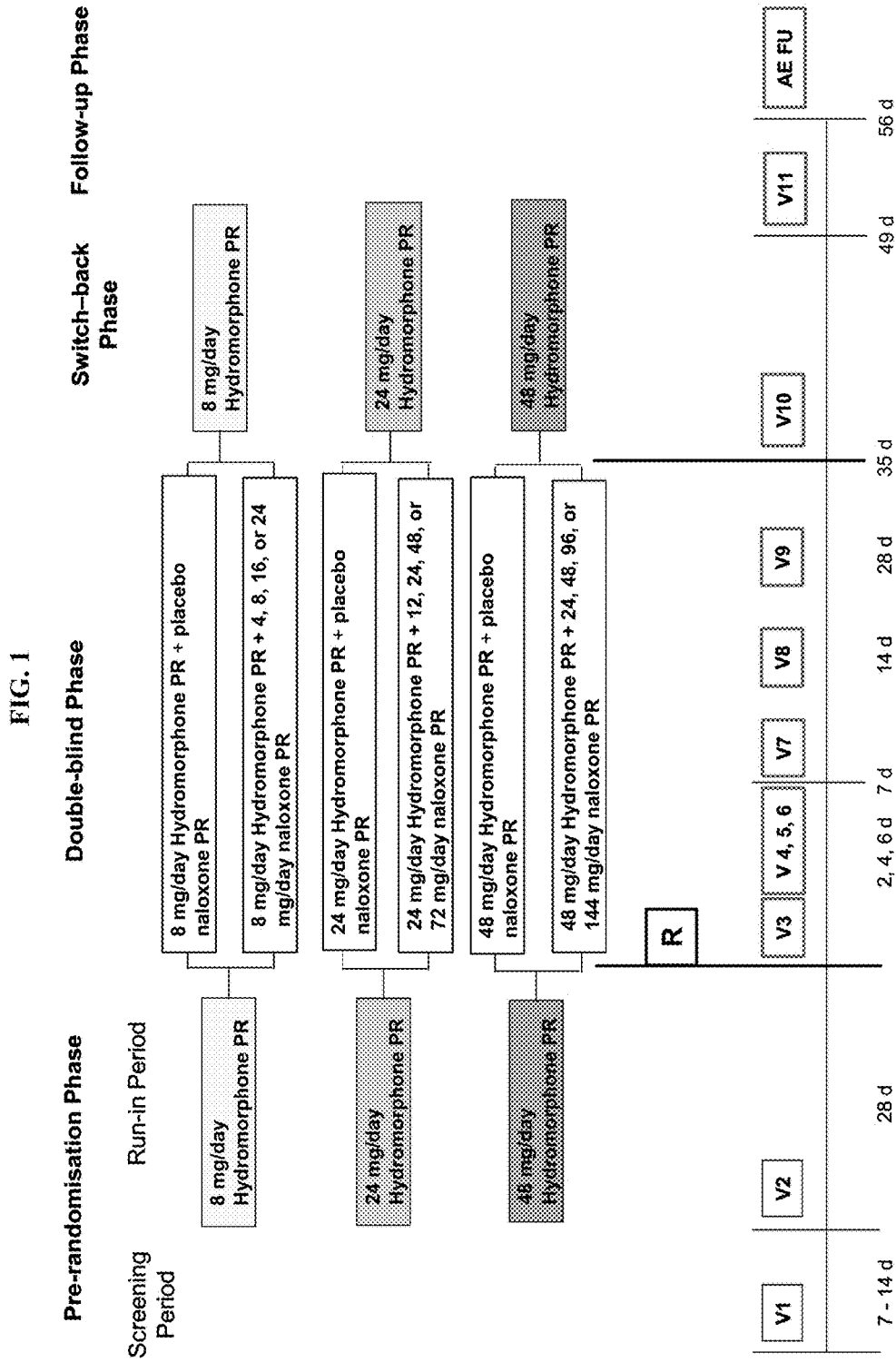
FIG. 1 illustrates the design of study for assessing pain and bowel function index.

The present invention as illustratively described in the following may suitably be practiced in the absence of any element or elements, limitation or limitations, not specifically disclosed herein.

The present invention will be described with respect to particular aspects and embodiments and with reference to certain figures, but the invention is not limited thereto. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising of". If hereinafter e.g. a group is defined to comprise at least a certain number of elements, this is to be understood to always also disclose a group which preferably consists only of these elements. If an aspect or embodiment of the invention is defined to comprise at least certain compositional, structural and/or functional features, this is to be understood to always also disclose an aspect and embodiment, which preferably consists only of these features.

Where an indefinite or definite article is used when referring to a singular noun, e.g. "a", "an" or "the", this includes a plural of that noun unless something else is specifically stated.

In the context of the present invention the terms "about" or "approximately" denote an interval of accuracy that the person skilled in the art will understand to still ensure the technical effect of the feature in question. The term indicates deviation from the indicated numerical value of ±10%, and preferably of ±5%.

When the term "about" is used in the context of a weight ratio such as e.g. that a composition comprises hydromorphone or a pharmaceutically acceptable salt thereof, and naloxone or a pharmaceutically acceptable salt thereof in a weight ratio of about 1:1 or about 1:2 this always includes a deviation of ±0.3, preferably ±0.2 and more preferably ±0.1 from the indicated ratio. A ratio of about 1:2 thus includes ratios of from 1:1.7 to 1:2.3, preferably from 1:1.8 to 1:2.2 and more preferably from 1:1.9 to 1:2.1.

The term "in vitro release" and its grammatical variations as well as similar expressions refer to the release rate, by which a pharmaceutically active agent, e.g. hydromorphone HCl or naloxone HCl is released from a pharmaceutical composition when the in vitro release rate is tested by the paddle method according to the European Pharmacopeia as described in as described in the Ph. Eur. 2.9.3 6$^{th}$ edition. The paddle speed is typically set at 100 rpm in 900 ml simulated gastric fluid (SGF) dissolution medium with pH 1.2. Aliquots of the dissolution media are withdrawn at the respective time points and analyzed by HPLC with a C18 column, eluted with 30 mM phosphate buffer in acetonitrile (70:70; pH 2.9) with a flow rate of 1.0 ml/min and detected at 220 nm.

The term "Simulated Gastric Fluid, pH 1.2" refers to 0.1 N HCl, pH 1.2.

In the context of the present invention, the terms "immediate release" or "conventional release" refer to pharmaceutical compositions showing a release of the active substance(s), which is not deliberately modified by a special formulation design and/or manufacturing methods. For oral dosage forms this means that the dissolution profile of the active substance(s) depends essentially on its (theirs) intrinsic properties. Typically, the terms "immediate release" or "conventional release" refer to pharmaceutical compositions, which release in vitro >75% (by weight) of the pharmaceutically active agent(s) at 45 min.

In the context of the present invention, the terms "prolonged release" and "controlled release" are used interchangeably and refer to pharmaceutical compositions showing a slower release of the active agent(s) than that of an immediate release pharmaceutical composition administered by the same route. Prolonged or controlled release is achieved by a special formulation design and/or manufacturing method. Typically, the terms "prolonged release" and "controlled release" refer to pharmaceutical compositions which release in vitro ≤75% (by weight) of the pharmaceutically active agent(s) at 45 min. The terms "prolonged release" or "controlled release" thus typically refer to situation where the active agents are released from a pharmaceutical composition over prolonged periods of time, such as e.g. about 8, 10, 12, 14, 16, 18, 20, 22 or 24 hours.

The terms "prolonged release formulation" or "controlled release formulation" are used interchangeably and refer to a pharmaceutical composition including at least one prolonged release material or controlled release material, and at least hydromorphone and naloxone or pharmaceutically acceptable salts thereof, which have been formulated to achieve a prolonged release of the active agents as explained above. The terms "prolonged release material" and "controlled release material" can be used interchangeably.

In the context of the present invention, the terms "prolonged (or controlled) release formulation", "prolonged (or controlled) release pharmaceutical composition", and "prolonged (or controlled) release dosage form" are used interchangeably and preferably refer to compositions, which as a consequence of the prolonged release of the active agents are suitable for administration of the pharmaceutically active agents every 12 hours or every 24 hours, i.e. they provide for therapeutic efficacy for at least 12 or at least 24 hours. Such compositions are also commonly designated as twice-a-day or once-a-day compositions, respectively. Throughout the invention as described herein, prolonged release pharmaceutical compositions, which are suitable for administration every 12 hours, are particularly preferred. Given that the prolonged release pharmaceutical compositions of the present invention comprise a combination of hydromorphone or a pharmaceutically acceptable salt thereof and naloxone or a pharmaceutically acceptable salt thereof, the skilled person will understand that the term "suitable for administration every 12 hours" means that such a prolonged release pharmaceutical composition for a given dose, that is required by a patient, will allow treatment of pain over a period of 12 hours. The term "suitable for administration every 24 hours" correspondingly means that such a prolonged release pharmaceutical composition for a given dose that is required by a patient will allow treatment of pain over a period of 24 hours. The skilled person will further understand that pain treatment with opioids such as hydromorphone is a continuous treatment such that the treatment efficacy of e.g. at least 12 hours refers to a situation where a patient has been adjusted to a proper dose and is in steady state.

Prolonged release properties may be obtained by different means such as by a coating, which is then designated as a prolonged release coating, a matrix, which is then designated by as a prolonged release matrix, an osmotic structure of the pharmaceutical composition, or combinations thereof.

In order to obtain "prolonged or controlled release" properties, one of skill in the art typically uses materials, which are known to prolong the release from a dosage form comprising e.g. a prolonged release matrix and/or prolonged release coating.

Typical examples of such "prolonged or controlled release materials" are hydrophobic polymers such as ethyl cellulose, hydrophilic polymers such as hydroxypropyl cellulose, fatty alcohols, waxes and the like, and combinations thereof. The nature of the "prolonged or controlled release material" may depend on whether the release properties are attained by a "prolonged release matrix" or a "prolonged release coating". The term "prolonged release materials" thus describes both types of materials.

The term "prolonged release matrix material" indicates that a material is used for obtaining a prolonged release matrix. Likewise, the term "prolonged release coating material" indicates that a material is used for obtaining a prolonged release coating. It is to be understood that depending on the method of manufacture a prolonged release material can be used for making a prolonged release matrix and a prolonged release coating. Further, in order to be useful as a prolonged release material, a prolonged release material may need to be present in minimum amounts. The person skilled in the art is familiar with the nature and the amounts of prolonged release materials that are necessary to make e.g. a prolonged release matrix or prolonged release coating.

It is to be understood that a material will be considered to act as prolonged or controlled release material if the dissolution profile of the pharmaceutically active agent(s) is slowed down compared to an immediate or conventional release formulation.

In a "prolonged or controlled release matrix", the active agent(s) will be combined with the prolonged or controlled release matrix material such that the active agent is (are) embedded in a three-dimensional matrix structure, from which the active agent(s) is (are) released in the above described prolonged manner, e.g. over a period of about 6, 8, 10, or 12 hours. Even though hydromorphone or a pharmaceutically acceptable salt thereof and naloxone or a pharmaceutically acceptable salt thereof may be embedded separately into distinct prolonged release matrices, wherever reference is made to a controlled release matrix this always preferably relates to the scenario where hydromorphone or a pharmaceutically acceptable salt thereof and naloxone or a pharmaceutically acceptable salt thereof are embedded in the same prolonged or controlled release matrix.

Pharmaceutically acceptable excipients, which are used to adjust an already prolonged or controlled release to a specific profile, are not necessarily considered to be prolonged or controlled release materials. In the case of prolonged release or controlled release matrix formulations, such materials may include water-soluble, quickly dissolving components, which are embedded in the matrix and can be used to accelerate the release from a prolonged or controlled release matrix formulation by creating channels in, promoting swelling of or affecting slow disintegration of the matrix. Examples of such additional excipients are pore-formers.

It is to be understood that a prolonged release matrix or a controlled release matrix may consist only of the pharmaceutically active agent(s) and the prolonged or controlled release material, or may comprise in addition pharmaceutically acceptable excipients such as fillers, lubricants, glidants, etc. However, those materials that are responsible for prolonging the release of the active agent(s) and form part of the matrix structure will be considered as prolonged release matrix material.

Further a prolonged release matrix, regardless of whether it is made only of the active agents and prolonged release matrix material(s) or comprises additional excipients, may be combined with such excipients to form the actual dosage form, which is the pharmaceutical composition that will be ultimately administered to a patient. The prolonged or controlled release properties which are provided by a prolonged matrix will typically be measured on the actual dosage form, e.g. for tablets. However, if the dosage form consists e.g. of multiparticulate prolonged or controlled release matrix particles, which would, e.g., be filled into capsules or embedded into instantly disintegrating tablets, the prolonged or controlled release properties can be measured directly for those particles.

In a "prolonged release coating formulation" or "controlled release coating formulation", the "prolonged release material" or "controlled release material" are optionally disposed on the pharmaceutically active agents to form a diffusion barrier. Other than in prolonged release matrix formulation, the prolonged release coating does not form a three dimensional structure within which the actives are distributed. In some embodiments, as the term implies, the prolonged release coating forms a layer surrounding the actives that does not include the actives within. In other embodiments, some active can be located within the coating.

When it is mentioned that a prolonged release coating is disposed on pharmaceutically active agents, this is not to be construed as meaning that such a coating will necessarily be directly layered on such active pharmaceutically agents. Of course, if pharmaceutically active agents are layered on a carrier such as nu-pareil beads, the coating may be disposed directly thereon. However, the pharmaceutically active agents may also be first embedded in a polymer layer or e.g. a prolonged release matrix. Subsequently the prolonged release coating may be disposed on e.g. granules which comprise a prolonged release matrix or on tablets which are made from such granules by compression for example. A prolonged release coating may also be disposed on structures, where the active(s) is (are) embedded in a matrix structure which by way of its size and/or composition does not provide in itself substantial prolonged release properties, i.e., a non-prolonged release matrix.

Even though hydromorphone or a pharmaceutically acceptable salt thereof and naloxone or a pharmaceutically acceptable salt thereof may be coated separately with distinct prolonged release coatings, wherever reference is made to a controlled release coatings this always preferably relates to the scenario where hydromorphone or a pharmaceutically acceptable salt thereof and naloxone or a pharmaceutically acceptable salt thereof are covered by the same prolonged or controlled release coating.

A pharmaceutical composition with a controlled or prolonged release coating may be obtained by combining the pharmaceutically active agents with a carrier such as nonperil beads and disposing a prolonged release coating on said combinations. Such coating may be made from polymers such cellulose ethers with ethyl cellulose being preferred, acrylic resins, other polymers and mixtures thereof.

Pharmaceutically acceptable excipients, which are used to adjust an already prolonged or controlled release to a specific profile, are not necessarily considered to be prolonged or controlled release materials. In case of prolonged release or controlled release coating formulations such materials may include water-soluble, quickly dissolving components, which are embedded in the coating and can be used to accelerate the release from a prolonged or controlled release matrix formulation by creating channels or holes in the coating. Examples of such additional excipients are pore-formers.

It is further to be understood that the term "prolonged release matrix formulation" or "controlled release matrix formulation" does not exclude pharmaceutical compositions with a prolonged or controlled release matrix and an additional prolonged or controlled release coating being disposed on the matrix. Likewise the term "prolonged release coating formulation" or "controlled release coating formulation" does not exclude pharmaceutical compositions with a prolonged or controlled release coating which is disposed on a prolonged release matrix or a controlled release matrix.

For some embodiments, the term "prolonged release matrix dosage form" may indicate that the dosage form comprises a prolonged release matrix as the sole structure being responsible for prolonging the release. This, however, does not exclude that the dosage form may comprise an immediate release portion as described hereinafter.

For some embodiments, the term "prolonged release coating dosage form" may indicate that the dosage form comprises a prolonged release coating as the sole structure being responsible for prolonging the release. This, however, does not exclude that the dosage form may comprise an immediate release portion as described hereinafter.

The release rates indicated hereinafter refer to the oral solid dosage form such as a monolithic tablet, a capsule or multi-particulates as they will be used for administration unless indicated otherwise.

Oral solid dosage forms may take the form of tablets, multiparticulates, and the like.

Multiparticulates refer to pharmaceutical compositions that are made from a plurality of particles such as granules and mini-tablets and where a unit dose, i.e. the amount of active(s) in a dosage form that will be administered to a patient, is distributed across the multiparticulates. In contrast, for monolithic tablets, a unit dose will be included in a single tablet.

In accordance with the present invention, mini-tablets are multiparticulate dosage forms, which comprise hydromorphone or a pharmaceutically acceptable salt thereof and naloxone or a pharmaceutically acceptable salt thereof in a matrix, which may be a prolonged or controlled release matrix or a carrier matrix structure not conveying prolonged release characteristics. Both matrices and in particular the matrix not conveying prolonged release characteristics may be coated with a prolonged release coating disposed thereon. They typically take a round to elliptical form with a thickness of about 1 to about 5 mm and a diameter of about 1 to 5 mm. A thickness and diameter of about 1 to about 4 mm, of about 1 to about 3 mm and of about 2 mm is also considered suitable.

Multiparticulates such as granules or mini-tablets may be either used directly or they may be filled into e.g. capsules. A capsule is considered to contain a multiparticulate dosage form as the capsule shell will not significantly if at all contribute to the prolonged release properties. Granules or mini-tablets can also be embedded in other excipients to form e.g. a tablet. It is important to note that tablets are only considered to be a multiparticulate dosage form if the tablet instantly, e.g. in less than 3 to 5 minutes disintegrates into the respective granules or mini-tablets such that the in vitro prolonged release characteristics will be actually measured on the granules or mini-tablets over course of time. If a monolithic tablet is produced by compressing e.g. granules with excipients and if such a tablet stays intact, i.e. does not disintegrate substantially in the course of the period where in vitro release rates are measured, such a monolithic tablet will not be considered as a multiparticulate dosage form.

Thus, the term "multiparticulates" refers to compositions made from a plurality of particles comprising hydromorphone or a pharmaceutically acceptable salt thereof and naloxone or a pharmaceutically acceptable salt thereof, such as granules or mini-tablets. If such multiparticulates are filled into capsules or embedded into tablets that quickly disintegrate into the respective multiparticulates, these carrier capsules or tablets will also be considered multiparticulates. In contrast, the term "monolithic tablet" is used to describe dosage forms that are not multiparticulate dosage forms.

The particles of multiparticulates may all comprise a combination of hydromorphone or a pharmaceutically acceptable salt hereof and naloxone or a pharmaceutically acceptable salt thereof and provide for prolonged release of the active agents. In an alternative, the particles may comprise prolonged release formulations of either hydromorphone or a pharmaceutically acceptable salt thereof or naloxone or a pharmaceutically acceptable salt thereof and then be combined in e.g. capsules to provide a mixture of particles. The particles may all comprise a prolonged matrix and/or prolonged coating. In an alternative, some particles may comprise hydromorphone or a pharmaceutically acceptable salt thereof in a prolonged release matrix and other particles may comprise hydromorphone or a pharmaceutically acceptable salt thereof surrounded by a prolonged release coating. The particles may then be combined in e.g. capsules to obtain the multiparticulate composition. The particles of multiparticulate compositions may also either each comprise an additional immediate release phase of hydromorphone or a pharmaceutically acceptable salt thereof, e.g. in the form of an immediate release top coating or an immediate release phase may be provided in the form of additional immediate release particles.

In one embodiment that may be preferred the prolonged release dosage forms in accordance with the invention comprise multiparticulates in the form of mini-tablets, in which both hydromorphone or a pharmaceutically acceptable salt thereof and naloxone or a pharmaceutically acceptable salt thereof are embedded in the same matrix particles with a controlled release coating disposed thereon. The matrix structure, even though it is made from prolonged or controlled release materials, will not or at least not significantly contribute to the prolonged release of the active agents. The reason is that, due to the small size of matrix particles of these multiparticulates and/or mini-tablets, the actives will be located to a considerable extent at the surface and will thus be basically instantly released. The matrix structure mainly serves to provide storage stability for hydromorphone or a pharmaceutically acceptable salt thereof and naloxone or a pharmaceutically acceptable salt thereof and the prolonged release properties are conveyed largely, if not completely by a controlled release coating on each of these mini-tablets.

The term "heat treatment" is used in the context of heat treating a prolonged release matrix formulation. The term "curing" is used in the context of heat treating a prolonged release coating formulation and relates to the effects of heat on the coalescence of the coating. If a composition comprises a prolonged release matrix and a prolonged release coating, the term "heat treatment" or "heat treated" denotes that the prolonged release matrix has been heat treated before the prolonged release coating was applied.

The present invention as disclosed herein with respect to all aspects and embodiments is meant to encompass the use of any pharmaceutically acceptable salt of hydromorphone and naloxone. Any embodiment of the invention referring to hydromorphone and naloxone is also meant to refer to salts and preferably the hydrochloride salts thereof unless indicated otherwise.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like, as well as any combination of these.

If in the following, reference is made to a pharmaceutically active agent such as hydromorphone, this always also includes the reference to a pharmaceutically acceptable salt of the free base of this pharmaceutically active agent unless it is specifically indicated that the reference to the pharmaceutically active agent, such as use of the term "hydromorphone" should only refer to the free base.

The use of the hydrochloride salts of both hydromorphone and naloxone is preferred for all aspects and embodiments as discussed hereinafter.

In a preferred embodiment, the pharmaceutical dosage forms comprise hydromorphone or a pharmaceutically acceptable salt thereof and naloxone or a pharmaceutically acceptable salt thereof as the sole pharmaceutically active agents.

The pharmaceutical compositions may comprise about 1 to about 64 mg such as about 1 mg, about 2 mg, about 4 mg, about 8 mg, about 12 mg, about 16 mg, about 24 mg, about 32 mg, about 40 mg, about 48 mg or about 64 mg hydromorphone hydrochloride or equimolar amounts of any other pharmaceutically acceptable salt including but not limited to hydrates and solvates, or of the free base. Where reference is made to amounts of hydromorphone hydrochloride, another hydromorphone salt, or hydromorphone free base, this relates to the anhydrous form of hydromorphone hydrochloride, the other salt, or the free base, respectively. If a hydrated version of hydromorphone hydrochloride, another salt, or the free base is used, this will be used in an amount equivalent to the afore-mentioned amounts of the anhydrous form of hydromorphone hydrochloride, the other salt, or the free base, respectively.

The pharmaceutical compositions may comprise about 1 to about 128 mg, such as about 1 mg, about 2 mg, about 4 mg, about 8 mg, about 12 mg, about 16 mg, about 24 mg, about 32 mg, about 48 mg, about 64 mg, about 96 mg, or about 128 mg of naloxone hydrochloride or equimolar amounts of any other pharmaceutically acceptable salt, derivative or form including but not limited to hydrates and solvates, or of the free base. Where reference is made to amounts of naloxone hydrochloride or another naloxone salt, this relates to the anhydrous form of naloxone hydrochloride or the other salt, respectively. If a hydrated version of naloxone hydrochloride or another salt is used, this will be used in an amount equivalent to the afore-mentioned amounts of the anhydrous form of naloxone hydrochloride or the other salt, respectively.

As will be apparent from the ensuing description, a ratio range of about 2:1 to about 1:3 and in particular ratios of about 2:1, about 1:1, about 1:2 and about 1:3 of hydromorphone or a pharmaceutically acceptable salt thereof and naloxone or a pharmaceutically acceptable salt thereof have been tested for the specific combination of hydromorphone HCl and naloxone HCl, e.g. for combinations of 8 mg hydromorphone HCl and 4 mg naloxone HCl, 8 mg hydromorphone HCl and 8 mg naloxone HCl, 8 mg hydromorphone HCl and 16 mg naloxone HCl, and 8 mg hydromorphone HCl and 24 mg naloxone HCl. Other specific combinations can be taken from Table 5. It is to be understood that, wherever reference is made to a combination, a pharmaceutical composition, a solid oral prolonged release pharmaceutical composition, etc. comprising hydromorphone or a pharmaceutically acceptable salt thereof and naloxone or a pharmaceutically acceptable salt thereof in a specific weight ratio such as about 1:2, this weight ratio refers to the weight ratio as determined for hydromorphone HCl and naloxone HCl. If other pharmaceutically acceptable salts, or the free base of hydromorphone and naloxone are used, the weight ratios as mentioned herein will have to be adapted accordingly. Thus, an about 1:2 ratio of 4 mg hydromorphone HCl and 8 mg naloxone HCl translates into a weight ratio of about 1:2.03 if corresponding amounts of the free base of hydromorphone, i.e. 3.55 mg and naloxone, i.e. 7.2 mg are used. An about 1:2 ratio of 4 mg hydromorphone HCl and 8 mg naloxone HCl correspondingly translates into a weight ratio of about 1:2.47, if corresponding amounts of the free base of hydromorphone, i.e. 3.55 mg and of naloxone HCl dihydrate, i.e. 8.79 mg naloxone are used.

The indication of a weight ratio range of about 1:1 to about 1:2 covers weight ratios of about 1:1, about 1:1.1, about 1:1.2, about 1:1.3, about 1:1.4, about 1:1.5, about 1:1.6, about 1:1.7, about 1:1.8, about 1:1.9, or about 1:2.0.

In a first aspect, the invention relates to a solid oral prolonged release pharmaceutical composition comprising hydromorphone or a pharmaceutically acceptable salt thereof and naloxone or a pharmaceutically acceptable salt thereof in a weight ratio corresponding to about 1:2 of hydromorphone HCl:naloxone HCl, hydromorphone or a pharmaceutically acceptable salt thereof in amount corresponding to about 24 mg of hydromorphone hydrochloride, and naloxone or a pharmaceutically acceptable salt thereof in an amount corresponding to about 48 mg of naloxone hydrochloride, wherein the formulation is suitable for administration every twelve hours.

In a second aspect, the invention relates to a solid oral prolonged release pharmaceutical composition comprising hydromorphone or a pharmaceutically acceptable salt thereof and naloxone or a pharmaceutically acceptable salt thereof in a weight ratio corresponding about 1:1 of hydromorphone HCl:naloxone HCl, hydromorphone or a pharmaceutically acceptable salt thereof in amount corresponding to about 24 mg of hydromorphone hydrochloride, and naloxone or a pharmaceutically acceptable salt thereof in an amount corresponding to about 24 mg of naloxone hydrochloride, wherein the formulation is suitable for administration every twelve hours.

In a third aspect, the pharmaceutical compositions as described for the first and second aspect are for use in the treatment of pain.

In a fourth aspect, the pharmaceutical compositions as described for the first and second aspect are for use in the treatment of pain and prevention and/or reduction of opioid-induced constipation.

In a fifth aspect, the pharmaceutical compositions as described for the first and second aspect are for use in the treatment of pain in patients experiencing opioid-induced constipation as a consequence of treatment with an opioid in the absence of an opioid antagonist.

In a sixth aspect, the invention relates to a solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain in a patient.

In a seventh aspect, the invention relates to a solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain and preventing and/or reducing opioid-induced constipation in a patient.

In an eighth aspect, the invention relates to a solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain in a patient, wherein the patient experiences opioid-induced constipation as a consequence of treatment with an opioid in the absence of an opioid antagonist.

In a first preferred embodiment of this sixth, seventh, and eighth aspect, the administered pharmaceutical composition comprises hydromorphone or a pharmaceutically acceptable salt thereof in an amount corresponding to from and including about 2 mg up to and including about 32 mg of hydromorphone hydrochloride, and naloxone or a pharmaceutically acceptable salt thereof in an amount corresponding to from and including about 2 mg up to and including about 64 mg of naloxone hydrochloride, wherein the prolonged release pharmaceutical composition is suitable for administration every 12 hours. For example, such solid oral prolonged release pharmaceutical composition may comprise hydromorphone or a pharmaceutically acceptable salt thereof in an amount corresponding to about 2 mg, about 4 mg, about 8 mg, about 12 mg, about 16 mg, about 24 mg, or about 32 mg, (including amount ranges between any of these amounts) of hydromorphone hydrochloride and naloxone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of naloxone hydrochloride, wherein the prolonged release pharmaceutical composition is suitable for administration every 12 hours.

In a second preferred embodiment of this sixth, seventh, and eighth aspect, the administered pharmaceutical composition comprises hydromorphone or a pharmaceutically acceptable salt thereof in an amount corresponding to from and including about 4 mg up to and including about 24 mg of hydromorphone hydrochloride, and naloxone or a pharmaceutically acceptable salt thereof in an amount corresponding to from and including about 4 mg up to and including about 48 mg of naloxone hydrochloride, wherein the pharmaceutical composition comprises hydromorphone or a pharmaceutically acceptable salt thereof and naloxone or a pharmaceutically acceptable salt thereof in a weight ratio corresponding to about 1:1 or about 1:2 of hydromorphone HCl:naloxone HCl, and wherein the prolonged release pharmaceutical composition is suitable for administration every 12 hours. For example, such solid oral prolonged release pharmaceutical compositions may comprise hydromorphone or a pharmaceutically acceptable salt thereof in an amount corresponding to about 4 mg, about 8 mg, about 12 mg, about 16 mg, or about 24 mg (including amount ranges between any of these amounts) of hydromorphone hydrochloride and naloxone or a pharmaceutically acceptable salt thereof in an amount corresponding to about 4 mg, about 8 mg, about 12 mg, about 16 mg, about 24 mg, about 32 mg, or about 48 mg (including amount ranges between any of these amounts) of naloxone hydrochloride, wherein the prolonged release pharmaceutical composition is suitable for administration every 12 hours.

In a ninth aspect, the invention relates to a combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain in a patient, by orally administering hydromorphone or a pharmaceutically acceptable salt thereof in a daily amount corresponding to and including about 2 mg up to and including about 64 mg, of hydromorphone hydrochloride, and naloxone or a pharmaceutically acceptable salt thereof in a daily amount corresponding to and including about 2 mg up to and including about 64 mg of naloxone hydrochloride. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of naloxone hydrochloride.

In a 10$^{th}$ aspect, the invention relates to a combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 64 mg of naloxone hydrochloride. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of naloxone hydrochloride.

In an 11$^{th}$ aspect, the invention relates to a combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 64 mg of naloxone hydrochloride, and wherein the patient experiences opioid-induced constipation as a consequence of treatment with an opioid in the absence of an opioid antagonist. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of naloxone hydrochloride.

In a first preferred embodiment of this ninth, 10$^{th}$, and 11$^{th}$ aspect, hydromorphone or a pharmaceutically acceptable salt thereof is administered in a daily amount corresponding to from and including about 8 mg up to and including about 24 mg of hydromorphone hydrochloride, and naloxone or a pharmaceutically acceptable salt thereof is administered in a daily amount corresponding to from and including about 8 mg up to and including about 24 mg of naloxone hydrochloride. For example, such administration comprises administering per day hydromorphone or a pharmaceutically acceptable salt thereof in an amount corresponding to from about 8 mg, about 12 mg, about 16 mg, or about 24 mg (including amount ranges between any of these amounts) of hydromorphone hydrochloride and administering per day naloxone or a pharmaceutically acceptable salt thereof in an amount corresponding to about 8 mg, about 12 mg, about 16 mg, or about 24 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio corresponding to about 1:1 of hydromorphone HCl:naloxone HCl may be provided in the form of a solid, oral prolonged release pharmaceutical composition, which is suitable for administration every 12 or 24 hours.

In a second preferred embodiment of this ninth, 10$^{th}$, and 11$^{th}$ aspect, hydromorphone or a pharmaceutically acceptable salt thereof is administered every 12 hours in an amount corresponding to from and including about 4 mg up to and including about 12 mg of hydromorphone hydrochloride such as about 4 mg, about 8 mg, or about 12 mg (including amount ranges between any of these amounts) of hydromorphone hydrochloride, and naloxone or a pharmaceutically acceptable salt thereof is administered concomitantly every 12 hours in an amount corresponding to from and including about 4 mg up to and including about 12 mg of naloxone hydrochloride such as about 4 mg, about 8 mg, or about 12 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio of about 1:1 may be provided in the form of a solid, oral prolonged release pharmaceutical composition, which is suitable for administration every 12 hours. Such a solid, oral prolonged release pharmaceutical composition would comprise e.g. 12 mg hydromorphone HCl and 12 mg naloxone HCl.

In a $12^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a $13^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a $14^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride, and wherein the patient experiences opioid-induced constipation as a consequence of treatment with an opioid in the absence of an opioid antagonist. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a first preferred embodiment of this $12^{th}$, $13^{th}$, and $14^{th}$ aspect, hydromorphone or a pharmaceutically acceptable salt thereof is administered in a daily amount corresponding to from and including about 8 mg up to and including about 48 mg of hydromorphone hydrochloride, and naloxone or a pharmaceutically acceptable salt thereof is administered in a daily amount corresponding to from and including about 16 mg up to and including about 96 mg of naloxone hydrochloride. For example, such administration comprises administering per day hydromorphone or a pharmaceutically acceptable salt thereof in an amount corresponding to from about 8 mg, about 12 mg, about 16 mg, about 24 mg, or about 48 mg (including amount ranges between any of these amounts) of hydromorphone hydrochloride and administering per day naloxone or a pharmaceutically acceptable salt thereof in an amount corresponding to about 16 mg, about 24 mg, about 32 mg, or about 96 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio corresponding to about 1:2 of hydromorphone HCl:naloxone HCl may be provided in the form of a solid, oral prolonged release pharmaceutical composition, which is suitable for administration every 12 or 24 hours.

In a second preferred embodiment of this $12^{th}$, $13^{th}$, and $14^{th}$ aspect, hydromorphone or a pharmaceutically acceptable salt thereof is administered every 12 hours in an amount corresponding to from and including about 4 mg up to and including about 24 mg of hydromorphone hydrochloride such as about 4 mg, about 8 mg, about 12 mg, or about 24 mg (including amount ranges between any of these amounts) of hydromorphone hydrochloride, and naloxone or a pharmaceutically acceptable salt thereof is administered concomitantly every 12 hours in an amount corresponding to from and including about 8 mg up to and including about 48 mg of naloxone hydrochloride such as about 8 mg, about 16 mg, about 24 mg, or about 48 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio of about 1:2 may be provided in the form of a solid, oral prolonged release pharmaceutical composition, which is suitable for administration every 12 hours. Such a solid, oral prolonged release pharmaceutical composition would comprise e.g. 24 mg hydromorphone HCl and 48 mg naloxone HCl.

In a 15$^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride.

In a 16$^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride.

In a 17$^{th}$ aspect, the invention relates to a combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride, wherein the patient experiences opioid-induced constipation as a consequence of treatment with an opioid in the absence of an opioid antagonist.

In a first preferred embodiment of this 15$^{th}$, 16$^{th}$, and 17$^{th}$ aspect, the combination comprising hydromorphone or a pharmaceutically acceptable salt thereof and naloxone or a pharmaceutically acceptable salt thereof in a weight ratio of about 1:2 may be provided in the form of a solid, oral prolonged release pharmaceutical composition, which is suitable for administration every 24 hours.

In a second preferred embodiment of this 15$^{th}$, 16$^{th}$, and 17$^{th}$ aspect, the combination comprising hydromorphone or a pharmaceutically acceptable salt thereof and naloxone or a pharmaceutically acceptable salt thereof in a weight ratio corresponding to about 1:2 of hydromorphone HCl:naloxone HCl may be provided in the form of a solid, oral prolonged release pharmaceutical composition, which is suitable for administration every 12 hours. Such a solid, oral prolonged release pharmaceutical composition would comprise e.g. 24 mg hydromorphone HCl and 48 mg naloxone HCl.

In an 18$^{th}$ aspect, the invention relates to a combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain in a patient, by orally administering hydromorphone or a pharmaceutically acceptable salt thereof in a daily amount corresponding to and including about 2 mg up to and including about 64 mg, of hydromorphone hydrochloride, and naloxone or a pharmaceutically acceptable salt thereof in a daily amount corresponding to and including about 2 mg up to and including about 128 mg of naloxone hydrochloride. The maximum daily amount of hydromorphone HCl preferably will not exceed 64 mg. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a 19$^{th}$ aspect, the invention relates to a combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 128 mg of naloxone hydrochloride. The maximum daily amount of hydromorphone HCl preferably will not exceed 64 mg. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a 20$^{th}$ aspect, the invention relates to a combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 128 mg of naloxone hydrochloride, and wherein the patient experiences opioid-induced constipation as a consequence of treatment with an opioid in the absence of an opioid antagonist. The maximum daily amount of hydromorphone HCl preferably will not exceed 64 mg. For example, such administration comprises administering per day hydromorphone or a pharmaceutically acceptable salt thereof in an amount corresponding to about 2 mg, about 4 mg, about 8 mg, about 12 mg, about 16 mg, about 24 mg, about 32 mg, about, 48 mg, or about 64 mg (including amount ranges between any of these amounts) of hydromorphone hydrochloride and administering per day naloxone or a pharmaceutically acceptable salt thereof in an amount corresponding to about 2 mg, about 4 mg, about 8 mg, about 12 mg, about 16 mg, about 24 mg, about 32 mg, about, 48 mg, about 64 mg, or about 128 mg (including amount ranges between any of these amounts) of naloxone hydrochloride.

In a first preferred embodiment of this $18^{th}$, $19^{th}$, and $20^{th}$ aspect, hydromorphone or a pharmaceutically acceptable salt thereof is administered in a daily amount corresponding to from and including about 8 mg up to and including about 48 mg of hydromorphone hydrochloride, and naloxone or a pharmaceutically acceptable salt thereof is administered in a daily amount corresponding to from and including about 8 mg up to and including about 96 mg of naloxone hydrochloride. For example, such administration comprises administering per day hydromorphone or a pharmaceutically acceptable salt thereof in an amount corresponding to from about 8 mg, about 12 mg, about 16 mg, about 24 mg, or about 48 mg (including amount ranges between any of these amounts) of hydromorphone hydrochloride and administering per day naloxone or a pharmaceutically acceptable salt thereof in an amount corresponding to about 8 mg, about 12 mg, about 16 mg, about 24 mg, about 32 mg, about 48 mg, or about 96 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio range corresponding to about 1:1 to about 1:2 of hydromorphone HCl:naloxone HCl may be provided in the form of a solid, oral prolonged release pharmaceutical composition, which is suitable for administration every 12 or 24 hours.

In a second preferred embodiment of this $12^{th}$, $13^{th}$, and $14^{th}$ aspect, hydromorphone or a pharmaceutically acceptable salt thereof is administered every 12 hours in an amount corresponding to from and including about 4 mg up to and including about 24 mg of hydromorphone hydrochloride such as about 4 mg, about 8 mg, about 12 mg, about 16 mg, or about 24 mg (including amount ranges between any of these amounts) of hydromorphone hydrochloride, and naloxone or a pharmaceutically acceptable salt thereof is administered concomitantly every 12 hours in an amount corresponding to from and including about 4 mg up to and including about 48 mg of naloxone hydrochloride such as about 4 mg, about 8 mg, about 12 mg, about 16 mg, about 24 mg, about 32 mg, or about 48 mg (including amount ranges between any of these amounts) of naloxone hydrochloride. To this end the combination comprising hydromorphone or a pharmaceutically acceptable salt thereof and naloxone or a pharmaceutically acceptable salt thereof in a weight ratio range of about 1:1 to about 1:2 may be provided in the form of a solid, oral prolonged release pharmaceutical composition, which is suitable for administration every 12 hours.

If in the above mentioned third to $20^{th}$ aspect, reference is made to a composition, combination etc. for use in e.g. the treatment of pain, this is to be considered to also disclose the use of such a composition, combination etc. in the manufacture of a medicament for treatment of pain or a method of treating pain in a patient by administering such a composition, combination, etc.

By way of example the subject matter of the above $15^{th}$ aspect also relates to the use of a combination of hydromorphone or a pharmaceutically acceptable salt thereof and naloxone or a pharmaceutically acceptable salt thereof in a weight ratio corresponding to about 1:2 of hydromorphone HCl:naloxone HCl in the manufacture of a medicament for the oral treatment of pain in a patient by administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride. It also relates to a method of treating pain in a patient in need thereof by administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride, wherein the combination comprises hydromorphone or a pharmaceutically acceptable salt thereof and naloxone or a pharmaceutically acceptable salt thereof in a weight ratio corresponding to about 1:2 of hydromorphone HCl:naloxone HCl.

The pharmaceutical compositions, combination, etc. as contemplated herein may not only be for use in the treatment of pain and preventing and/or reducing opioid-induced constipation, but may also allow to reduce or avoid a food effect.

The term "food effect" generally refers to the situation that a pharmaceutical composition displays different bioavailability when taken by subjects in the fasted or fed state. A pharmaceutical composition, combination, etc. as contemplated herein is considered to show no, or at least no significant food effect if the pharmacokinetic parameters, i.e. AUC (area under the curve), $C_{max}$ (maximum plasma concentration) and/or $T_{max}$ (time to maximum plasma concentration) obtained with the pharmaceutical composition, combination etc. in the fed state fulfills the bioequivalence criteria vs. the pharmacokinetic parameters, i.e. AUC (area under the curve), $C_{max}$ (maximum plasma concentration) and/or $T_{max}$ (time to maximum plasma concentration) obtained with the pharmaceutical composition, combination etc. in the fasted state (see in this respect "Guideline on the Investigation of Bioequivalence" by the EMA, CPMP/EWP/QWP/1401/98 of 20 Jan. 2010). In order to determine a potential effect of food, subjects may take the pharmaceutical composition, combination, etc. either with or without a standardized meal and adhere to the same fasting conditions before taking the meal and pharmaceutical composition, combination, etc. Subjects in the fed state may thus e.g. take a high fat meal which may be a high-fat (approximately 50 percent of total caloric content of the meal) and high-calorie (approximately 800 to 1000 kcal) meal such as a high-fat breakfast. Subjects in the fasted and fed state may e.g. fast from food for at least 8 hours prior to dosing. Subjects randomized to be administered a pharmaceutical composition, combination, etc. in a fed state may consume a high-fat breakfast in the 30 minutes before dosing.

It is contemplated that certain weight ratios of hydromorphone or a pharmaceutically acceptable salt thereof and naloxone or a pharmaceutically acceptable salt thereof within the weight ratio range corresponding to from about 1:1 to about 1:2 of hydromorphone HCl:naloxone HCl, such as the weight ratio corresponding to about 1:1 of hydromorphone HCl:naloxone HCl may avoid or at least reduce a food effect.

Pharmaceutical compositions, combinations, etc. comprising hydromorphone or a pharmaceutically acceptable salt thereof and naloxone or a pharmaceutically acceptable salt thereof within the weight ratio range corresponding to from about 1:1 to about 1:2 of hydromorphone HCl:naloxone HCl, such as the weight ratio corresponding to about 1:1 of hydromorphone HCl:naloxone HCl may thus allow for treatment of pain and preventing and/or reducing opioid-induced constipation in patients taking the pharmaceutical compositions, combinations, etc. concomitantly, with food. Concomitant administration of pharmaceutical compositions, combinations, etc. with food relates e.g. to the situation that food is eaten within about 1 hour or within about 30 min before or within about 30 min, within about 1 hour, within about 2 hours or within about 3 hours after administration of pharmaceutical compositions, combinations, etc. Pharmaceutical compositions, combinations, etc. comprising hydromorphone or a pharmaceutically acceptable salt thereof and naloxone or a pharmaceutically acceptable salt thereof within the weight ratio range corresponding to from about 1:1 to about 1:2 of hydromorphone HCl:naloxone HCl, such as the weight ratio corresponding to about 1:1 of hydromorphone HCl:naloxone HCl, which have no or at least no substantial food effect may also be used for treatment of pain and/or reducing opioid-induced constipation in patients independent of whether these have eaten food or not. Pharmaceutical compositions, combinations, etc. comprising hydromorphone or a pharmaceutically acceptable salt thereof and naloxone or a pharmaceutically acceptable salt thereof within the weight ratio range corresponding to from about 1:1 to about 1:2 of hydromorphone HCl:naloxone HCl, such as the weight ratio corresponding to about 1:1 of hydromorphone HCl:naloxone HCl, which have no or at least no substantial food effect may further be used for treatment of pain and/or reducing opioid-induced constipation in patients which may require the concomitant intake of food.

If in the above mentioned ninth to $20^{th}$ aspect, reference is made to a combination comprising hydromorphone or a pharmaceutically acceptable salt thereof and naloxone or a pharmaceutically acceptable salt thereof, this refers to the situation where hydromorphone or a pharmaceutically acceptable salt thereof and naloxone or a pharmaceutically acceptable salt thereof are provided in the same dosage form, e.g. tablet, capsule, etc. or where hydromorphone or a pharmaceutically acceptable salt thereof and naloxone or a pharmaceutically acceptable salt thereof are provided in separate dosage forms, e.g. tablets, capsules, etc. In both scenarios, it is preferred that the dosage forms are prolonged release dosage forms. It can be particularly preferred that a combination of hydromorphone or a pharmaceutically acceptable salt thereof and naloxone or a pharmaceutically acceptable salt thereof are provided within the same prolonged release dosage form as this may ensure that the selected weight ratios, e.g. a 1:1 or 1:2, ratio are maintained during the passage of the actives throughout the gastrointestinal system.

Independent of whether hydromorphone or a pharmaceutically acceptable salt thereof and naloxone or a pharmaceutically acceptable salt thereof are provided in the same dosage form or in separate dosage forms, it may be preferred that both hydromorphone or a pharmaceutically acceptable salt thereof and naloxone or a pharmaceutically acceptable salt thereof are released with substantially the same in vitro release rates. The term "substantially the same in vitro release rate" refers to the situation that the in vitro release rate of naloxone or a pharmaceutically acceptable salt thereof does not deviate by more than about 20%, preferably by no more than about 15%, more preferably by no more than 10% from the in vitro release profile of hydromorphone or a pharmaceutically acceptable salt thereof if tested by the same method. A deviation of no more than 20%, 15%, or 10% refers to an absolute deviation for the in vitro release of naloxone or a pharmaceutically acceptable salt thereof at a given point in time from the in vitro release of hydromorphone or a pharmaceutically acceptable salt at the same given point in time. Thus, if e.g. 30% hydromorphone HCl are released from a dosage form at 2 h, the release of e.g. naloxone HCl from the same dosage form will be considered to be substantially the same if the in vitro release of naloxone HCl at 2 h is within the range of 10% to 50%. Correspondingly if e.g. 40% hydromorphone HCl are released from a dosage form at 4 h, the release of e.g. naloxone HCl from the same dosage form will be considered to be substantially the same if the in vitro release of naloxone HCl at 4 h is within the range of 20% to 60%. Providing hydromorphone or a pharmaceutically acceptable salt thereof and naloxone or a pharmaceutically acceptable salt thereof in the same dosage form or in separate dosage forms, which provide substantially the same in vitro release of both active agents, may be an preferred embodiment as this may ensure that the selected weight ratios, e.g. a 1:1 or 1:2 ratio are maintained during the in vitro release period. Providing hydromorphone or a pharmaceutically acceptable salt thereof and naloxone or a pharmaceutically acceptable salt thereof in the same dosage form, which releases both hydromorphone or a pharmaceutically acceptable salt thereof and naloxone or a pharmaceutically acceptable salt thereof released with substantially the same in vitro release rates may be a particularly preferred embodiment.

Wherever reference is made above to the treatment of pain, this includes the treatment of moderate to severe pain and even most severe pain. The pharmaceutical compositions are thus, in some embodiments, for use in the treatment of pain, which can be adequately managed only with opioid analgesics. Pain may include acute and/or chronic pain and preferably chronic non-malignant or chronic malignant pain. Specific types of chronic non-malignant pain include chronic non-malignant visceral, neuropathic or bone pain. Specific types of chronic malignant pain include chronic malignant cancer, visceral, neuropathic or bone pain.

The pharmaceutical compositions, which are for use in the treatment of pain, are preferably used in patients who suffer in addition to pain from opioid-induced bowel dysfunction syndrome. Opioid bowel dysfunction syndrome may preferably be opioid-induced constipation. The pharmaceutical composition for use in treatment of pain can thus be used to concomitantly improve opioid-induced constipation in a patient undergoing treatment for pain. Alternatively, they can be used to concomitantly prevent opioid-induced constipation in a patient undergoing treatment for pain.

In all of the above mentioned aspects and preferred embodiments, the pharmaceutically active agents will most preferably be hydromorphone HCl and naloxone HCl. These solid oral prolonged release pharmaceutical compositions will preferably comprise about 4 mg of hydromorphone HCl and about 8 mg of naloxone HCl, about 8 mg of hydromorphone HCl and about 16 mg of naloxone HCl, about 12 mg of hydromorphone HCl and about 24 mg of naloxone HCl, about 16 mg of hydromorphone HCl and about 32 mg of naloxone HCl and about 24 mg of hydromorphone HCl and about 48 mg of naloxone HCl and be suitable for administration every 12 hours or every 24 hours with a 12 hourly composition being preferred. The solid oral prolonged release pharmaceutical compositions will alternatively preferably comprise about 4 mg of hydromorphone HCl and about 4 mg of naloxone HCl, about 8 mg of hydromorphone HCl and about 8 mg of naloxone HCl, about 12 mg of hydromorphone HCl and about 12 mg of naloxone HCl, about 16 mg of hydromorphone HCl and about 16 mg of naloxone HCl, and about 24 mg of hydromorphone HCl and about 24 mg of naloxone HCl and be suitable for administration every 12 hours or every 24 hours with a 12 hourly composition being preferred.

Other solid oral prolonged release pharmaceutical compositions may comprise about 5 mg of hydromorphone HCl and about 10 mg of naloxone HCl, about 6 mg of hydromorphone HCl and about 12 mg of naloxone HCl, about 7 mg of hydromorphone HCl and about 14 mg of naloxone HCl, about 9 mg of hydromorphone HCl and about 18 mg of naloxone HCl, about 10 mg of hydromorphone HCl and about 20 mg of naloxone HCl, about 11 mg of hydromorphone HCl and about 22 mg of naloxone HCl, about 13 mg of hydromorphone HCl and about 26 mg of naloxone HCl, about 14 mg of hydromorphone HCl and about 28 mg of naloxone HCl, about 15 mg of hydromorphone HCl and about 30 mg of naloxone HCl, about 17 mg of hydromorphone HCl and about 34 mg of naloxone HCl, about 18 mg of hydromorphone HCl and about 36 mg of naloxone HCl, about 19 mg of hydromorphone HCl and about 38 mg of naloxone HCl, about 20 mg of hydromorphone HCl and about 40 mg of naloxone HCl, about 21 mg of hydromorphone HCl and about 42 mg of naloxone HCl, about 22 mg of hydromorphone HCl and about 44 mg of naloxone HCl, and about 23 mg of hydromorphone HCl and about 46 mg of naloxone HCl. These compositions may be suitable for administration every 12 or every 24 hours with a 12 hourly composition being preferred. Other solid oral prolonged release pharmaceutical compositions may comprise about 5 mg of hydromorphone HCl and about 5 mg of naloxone HCl, about 6 mg of hydromorphone HCl and about 6 mg of naloxone HCl, about 7 mg of hydromorphone HCl and about 7 mg of naloxone HCl, about 9 mg of hydromorphone HCl and about 9 mg of naloxone HCl, about 10 mg of hydromorphone HCl and about 10 mg of naloxone HCl, about 11 mg of hydromorphone HCl and about 11 mg of naloxone HCl, about 13 mg of hydromorphone HCl and about 13 mg of naloxone HCl, about 14 mg of hydromorphone HCl and about 14 mg of naloxone HCl, about 15 mg of hydromorphone HCl and about 15 mg of naloxone HCl, about 17 mg of hydromorphone HCl and about 17 mg of naloxone HCl, about 18 mg of hydromorphone HCl and about 18 mg of naloxone HCl, about 19 mg of hydromorphone HCl and about 19 mg of naloxone HCl, about 20 mg of hydromorphone HCl and about 20 mg of naloxone HCl, about 21 mg of hydromorphone HCl and about 21 mg of naloxone HCl, about 22 mg of hydromorphone HCl and about 22 mg of naloxone HCl, and about 23 mg of hydromorphone HCl and about 23 mg of naloxone HCl. These compositions may be suitable for administration every 12 or every 24 hours with a 12 hourly composition being preferred.

As mentioned above, the prolonged release pharmaceutical compositions in accordance with the invention may comprise a prolonged release matrix, a prolonged release coating, or combinations thereof.

As regards the manufacturing and specific components of such prolonged release pharmaceutical compositions, hydromorphone or a pharmaceutically acceptable salt thereof and naloxone or a pharmaceutically acceptable salt thereof may thus be combined with a prolonged release material such that a prolonged release matrix and/or a prolonged release coating is formed.

The prolonged release material may be any material that is known to be capable of imparting controlled release properties on the active agent when being formulated e.g. into a prolonged release matrix. Such materials may be hydrophilic and/or hydrophobic materials such as gums, cellulose ethers, acrylic polymers, protein-derived materials, polyethylenoxides, polycaprilactones, etc.

Prolonged release matrix materials may also include fatty acids, fatty alcohols, glyceryl esters of fatty acids, polyethylene glycols, mineral and oils and waxes. Preferable fatty acids and fatty alcohols are those with a $C_{10}$ to $C_{30}$ chain, preferably with a $C_{12}$ to $C_{24}$ chain and more preferably with a $C_{14}$ to $C_{20}$ chain or a $C_{16}$ to $C_{20}$ chain. Materials such as stearyl alcohol, cetostearyl alcohol, cetyl alcohol, myristyl alcohol and polyalkylene glycols may be preferred. Waxes may be selected from natural and synthetic waxes such as beeswax, carnauba wax, etc. Oils may be vegetable oils and include for example castor oil.

The prolonged release matrix materials which may be considered in the context of the present invention may also be selected from cellulose ethers.

The term "cellulose ethers" comprises cellulose-derived polymers derivatized with at least alkyl and/or hydroxyalkyl groups which may be hydrophilic or hydrophobic.

For example, the prolonged release matrix material may be a hydrophilic hydroxy alkyl cellulose such as a hydroxy $C_1$-$C_6$ alkyl cellulose such as hydroxypropyl cellulose, hydroxypropylmethyl cellulose and particularly preferably hydroxyethyl cellulose.

Examples of hydrophobic cellulose ethers include e.g. ethyl cellulose. The use of ethyl cellulose may be preferred. Hydrophobic cellulose ethers such as ethyl cellulose may be particularly suitable for imparting alcohol resistance to pharmaceutical compositions.

A suitable material for prolonged release matrix formulations in accordance with the present invention may be selected from the group of acrylic resins. Such acrylic resins may be made from (meth)acrylic acid (co) polymers.

There are various types of (meth)acrylic acid (co)polymers available which may be characterized according to the nature of their residues such as neutral (meth)acrylic acid (co)polymers, (meth)acrylic acid (co)polymers with anionic residues or (meth)acrylic acid ester copolymers with cationic residues.

Neutral (meth)acrylic acid (co)polymers include polymers having 95 to 100% by weight of polymerized monomers having neutral residues. Monomers with neutral residues can be $C_1$-$C_4$ alkyl esters of acrylic or methacrylic acid such as methylmethacrylate, ethylmethacrylate, butylmethacrylate, methylacrylate, ethylacrylate and butylacrylate. For example, neutral (meth)acrylic acid (co)polymers may comprise 20 to 40% by weight ethylacrylate and 60 to 80% by weight methylmethacrylate. Such polymers are e.g. available under the trade name Eudragit® NE which is a copolymer of 30% by weight ethylacrylate and 70% by weight methylmethacrylate. This polymer is usually provided in the form of a 30% or 40% aqueous dispersion (Eudragit® NE 30 D, Eudragit® NE 40 D or Eudragit® NM 30 D).

(Meth)acrylic acid (co)polymers with functional anionic residues may be (meth)acrylic acid (co)polymers having 25 to 95% by weight of radically polymerized $C_1$ to $C_4$ alkyl esters of acrylic or methacrylic acid and 5 to 75% by weight of methacrylate monomers with an anionic group in the alkyl residue. $C_1$ to $C_4$ alkyl esters of acrylic or methacrylic acid are again methylmethacrylate, ethyl methacrylate, butylmethacrylate, methylacrylate, ethylacrylate and butylacrylate. A (meth)acrylate monomer with an anionic group in the alkyl residue may be for example acrylic acid and preferably methacrylic acid. Such methacrylic acid copolymers with an anionic functional group may comprise e.g. 40 to 60% by weight methacrylic acid and 60 to 40% by weight methylmethacrylate or 60 to 40% by weight ethyl acrylate. These types of polymers are available as Eudragit® L100/ Eudragit® L 12.5 or Eudragit® L 100-55/Eudragit® L 30 D-55, respectively.

(Meth)acrylic acid (co)polymers with functional cationic groups may be methacrylic acid copolymers with tertiary amino groups. Such polymers may comprise 30% to 80% by weight of radically polymerized $C_1$-$C_4$ alkyl esters of acrylic acid or methacrylic acid and 70 to 20% by weight methacrylate monomers with a tertiary amino group in the alkyl rest. A common (meth)acrylic acid (co)polymer with a tertiary amino group may comprise 20 to 30% by weight methylmethacrylate, 20 to 30% by weight butylmethacrylate and 60 to 40% by weight dimethylaminoethyl methacrylate. For example the commercially available Eudragit® E 100 comprises 25% by weight methylmethacrylate, 25% by weight butylmethacrylate and 50% by weight dimethylaminoethyl methacrylate. Another common commercially available polymer, Eudragit®E PO comprises copolymers of methylmethacrylate, butylmethacrylate and dimethylaminoethyl methacrylate in a ratio of 25:25:50.

Another type of (meth)acrylic acid (co)polymers with functional cationic groups is (meth)acrylic acid (co)polymers with a quaternary amino group. This type of (meth) acrylic acid (co)polymers typically comprises 50 to 70% of radically polymerized methylmethacrylate, 20 to 40% by weight of ethylacrylate and 12 to 2% by weight of 2-trimethylammoniumethyl methacrylate chloride. Such polymers are e.g. available under the trade names Eudragit®RS or Eudragit®RL.

For example, Eudragit®RS comprises radically polymerized units of 65% by weight methylmethacrylate, 30% by weight ethylacrylate and 5% by weight 2-trimethylammoniumethyl methacrylate chloride. Eudragit®RL comprises radically polymerized units of 60% by weight methylmethacrylate, 30% by weight ethylacrylate and 10% by weight 2-trimethylammoniumethyl methacrylate chloride.

The amount of prolonged release matrix material(s) in the prolonged release formulation may be of about 5 to 90% by weight, of about 10 to 70% by weight, of about 20 to 60% by weight, of about 20% to about 55% by weight, of about 25% to about 50% by weight, of about 25% to about 45% by weight and preferably of about 30 to about 40% by weight based on the weight of the pharmaceutical composition. The amount of prolonged release matrix material that is incorporated into the composition can be one way of adjusting the prolonged release properties. For example, if the amount of prolonged release material is increased, the release can be further prolonged. The aforementioned amounts refer to the overall content of prolonged release materials in a pharmaceutical composition. These amounts may thus refer to a mixture of various prolonged release materials such as a neutral (meth)acrylic acid (co)polymer, a hydrophobic cellulose ether and/or a fatty alcohol.

If cellulose ether is among the prolonged release matrix materials, it will typically be present in an amount of about 5% to about 50% by weight, of about 5% to about 45% by weight, of about 5% to about 40% by weight, of about 5% to about 35% by weight, of about 5% to about 30% by weight, of about 5% to about 25% by weight, of about 5% to about 20% by weight such as of about 5% by weight, of about 7% by weight, of about 10% by weight, of about 15% by weight, of about 18% by weight or of about 20% by weight based on the weight of the pharmaceutical composition.

If a fatty alcohol is among the prolonged release matrix materials, it will typically be present in an amount of about 5% to about 50% by weight, of about 5% to about 45% by weight, of about 5% to about 40% by weight, of about 5% to about 35% by weight, of about 10% to about 30% by weight, of about 10% to about 25% by weight such as of about 10% by weight, of about 15% by weight, of about 20% by weight or about 25% by weight based on the weight of the pharmaceutical composition.

If (meth)acrylic acid (co)polymer is among the prolonged release matrix materials, it will typically be present in an amount of about 5% to about 50% by weight, of about 5% to about 45% by weight, of about 5% to about 40% by weight, of about 5% to about 35% by weight, of about 10% to about 30% by weight, of about 10% to about 25% by weight such as of about 10% by weight, of about 15% by weight, of about 20% by weight or about 25% by weight based on the weight of the pharmaceutical composition.

The pharmaceutical compositions in accordance with the invention may also include pharmaceutically acceptable excipients such fillers, lubricants, binders, release rate modifiers, anti-tacking agents, etc.

Fillers which may also be designated as diluents may include e.g. lactose, preferably anhydrous lactose, glucose or saccharose, starches, their hydrolysates, microcrystalline cellulose, cellatose, sugar alcohols such as sorbitol or mannitol, polysoluble calcium salts like calcium hydrogen phosphate, dicalcium- or tricalcium phosphate and combinations of two or more of the above fillers.

It has been observed that the combination of hydromorphone and naloxone can be moisture sensitive in particular if cellulose ethers are used as prolonged release material. In view of this situation it can be preferred to use fillers which do not import moisture e.g. in the form of water. In preferred embodiments, one may thus use anhydrous fillers such as anhydrous lactose.

Lubricants can include highly dispersed silica, talcum, corn starch, magnesium oxide and magnesium- or calcium stearate, fats like hydrated castor oil, sodium stearyl fumarate and combinations of two or more of the above lubricants.

It can be preferred to use a combination of magnesium stearate and talcum as lubricants. It has been found that if appropriate amounts of these lubricants are chosen, one can e.g. improve flow properties of granules used for compressing.

It thus can be preferred to use a lubricant amount of about 0.5% to about 4% by weight, of about 0.7% to about 3% by weight, of about 1% to about 2% by weight such as of about 1.0% by weight, of about 1.1% by weight, of about 1.2% by weight, of about 1.3% by weight, of about 1.4% by weight, of about 1.5% by weight, of about 1.6% by weight, of about 1.7% by weight, of about 1.8% by weight, of about 1.9% by weight or of about 2.0% by weight based on the weight of the pharmaceutical composition. An amount of about 0.75% to about 1.25% by weight based on the weight of the pharmaceutical composition can be preferred, particularly if magnesium stearate and talc are used. The aforementioned amounts refer to the amount of all lubricants (i.e. including mixtures) in the composition.

Binders can include hydroxypropyl cellulose (HPC), hydroxypropyl methyl cellulose, polyvinyl pyrollidone, carbopol, and combinations thereof.

It can be preferred to use HPC as a binder as this may positively influence the hardness of the tablets.

It thus can be preferred to use a binder amount of about 1% to about 10% by weight, of about 2% to about 9% by weight, of about 3% to about 7% by weight, of about 3% to about 6% by weight, of about 4% to about 5% by weight such as of about 4.0% by weight, of about 4.1% by weight, of about 4.2% by weight, of about 4.3% by weight, of about 4.4% by weight, of about 4.5% by weight, of about 4.6% by weight, of about 4.7% by weight, of about 4.8% by weight, of about 4.9% by weight or of about 5.0% by weight based on the weight of the pharmaceutical composition. An amount of about 4.4% to about 5.0% by weight based on the weight of the pharmaceutical composition can be preferred, particularly of HPC is used as binder. The aforementioned amounts refer to the amount of all binders (i.e. including mixtures) in the composition.

It can be preferred to not use povidone as a binder.

Release rate modifiers are pharmaceutically acceptable excipients which may be used to tune the release which otherwise would be obtained using the prolonged release matrix materials, e.g. to accelerate the release or to further slow the release. Such release modifiers may be hydrophilic substances such as polyethyleneglycols, hydroxypropylmethylcellulose, hydroxyethylcellulose, and the like or hydrophobic substances such as oils, waxes and the like. Other release modifiers may include some the aforementioned (meth)acrylic acid (co)polymers such as polymers of the Eudragit® RLPO type or gums such as xanthan gum.

Release rate modifiers such as polymers of the Eudragit/®RLPO type, low molecular weight hydroxypropylmethylcellulose such Hypromellose K100M or xanthan gum may be preferred.

Such release rate modifiers may be present in an amount of about 1% to about 20% by weight, of about 2% to about 19% by weight, of about 3% to about 18% by weight, of about 4% to about 17% by weight, of about 5% to about 15% by weight such as of about 5% by weight, of about 6% by weight, of about 7% by weight, of about 8% by weight, of about 9% by weight, of about 10% by weight, of about 11% by weight, of about 12% by weight, of about 13% by weight, of about 14% by weight or of about 15% by weight based on the weight of the pharmaceutical composition. The aforementioned amounts refer to the amount of all release rate modifiers (i.e. including mixtures) in the composition.

It is to be understood that the functions of pharmaceutically acceptable excipients may be overlapping. For example, a spheronising agent such as microcrystalline cellulose can also be used as filler if appropriate amounts are chosen. Further, HPMC may not only act as release rate modifying agent but also as binder if e.g. used in prolonged release formulation with a coating.

Prolonged release pharmaceutical compositions with a prolonged release coating may be made from materials which are common in the art.

The prolonged release coating materials may thus be selected e.g. from (i) an alkylcellulose; (ii) an acrylic polymer; (iii) polyvinyl alcohol or (iv) mixtures thereof. Hydrophobic representatives of the afore-mentioned groups can be preferred. The coating may be applied in the form of an organic or aqueous solution or dispersion.

In some embodiments, the controlled release coating is derived from an aqueous dispersion of the hydrophobic controlled release material. The coated composition can then be cured.

In preferred embodiments, the controlled release coatings include a plasticizer such as those described herein below.

In certain embodiments, one may coat with an amount of coating material which is sufficient to obtain a weight gain level from about 2 to about 20%, e.g., about 2 to about 15% and preferably about 5 to about 10% such as 6%, 7%, 8% or 9% in order to obtain sufficiently prolong the release from the formulation.

Cellulosic materials and polymers, including alkyl celluloses are prolonged release materials well suited for coating substrates, e.g., beads, granules, tablets, etc. according to the invention. Simply by way of example, one preferred alkyl cellulosic polymer is ethyl cellulose One commercially available aqueous dispersion of ethyl cellulose is Aquacoat® such as Aquacoat® ECD30 (FMC Corp., Philadelphia, Pa., U.S.A.). Aquacoat is prepared by dissolving the ethyl cellulose in a water-immiscible organic solvent and then emulsifying the same in water in the presence of a surfactant and a stabilizer. After homogenization to generate submicron droplets, the organic solvent is evaporated under vacuum to form a pseudo latex.

Another aqueous dispersion of ethyl cellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

The prolonged release coating material can also be a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride) and glycidyl methacrylate copolymers.

The acrylic polymer may be comprised of one or more ammonium methacrylate copolymers. Ammonium methacrylate copolymers are well known in the art, and are described as fully polymerized copolymers of acrylic and methacrylic acid esters with a low content of quaternary ammonium groups. Typical examples include Eudragit® RS30D which is a low permeability ammonium methacrylate polymer and Eudragit®RL30D which is a high permeability ammonium methacrylate polymer. Eudragit RL and Eudragit RS are water swellable, and the amount of water absorbed by these polymers is pH-dependent, however, dosage forms coated with Eudragit RL and RS are pH-independent.

The acrylic coatings may comprise a mixture of two acrylic resin lacquers commercially available from Rohm Pharma under the Trade names Eudragit®RL30D and Eudragit®RS30D, respectively. The Eudragit®RL/RS dispersions of the present invention may be mixed together in any desired ration in order to ultimately obtain a prolonged-release formulation having a desirable dissolution profile.

Other polymers which can be used as a prolonged release coating materials if they are applied at sufficient amounts are e.g. hydrophilic polymers such as hydroxypropylmethylcellulose.

The above mentioned coatings may also be applied in combination. Further it is possible to influence the release properties of a dosage form by increasing the amount of the coating material and thus the thickness of the coating.

In embodiments of the present invention where the coating comprises an aqueous dispersion of a hydrophobic controlled release material, the inclusion of an effective amount of a plasticizer in the aqueous dispersion of hydrophobic material may further improve the physical properties of the prolonged release coating. For example, because ethyl cellulose has a relatively high glass transition temperature and may not form flexible films under normal coating conditions, it can be preferred to incorporate a plasticizer into an ethyl cellulose coating containing prolonged release coating before using the same as a coating material. Generally, the amount of plasticizer included in a coating solution is based on the concentration of the film-former, e.g., most often from about 1 to about 50% by weight of the film-former.

Examples of suitable plasticizers for ethyl cellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit®RL/RS lacquer solutions include polyethylene glycols, propylene glycol, diethyl phthalate, castor oil, and triacetin.

If one attempts to realize specific in vitro release rates, one can use combinations of the above mentioned measures. For example, if the release from a prolonged release matrix is deemed too fast because the matrix particles are so small that a substantial amount of active is placed on the surface of the particles and thus released immediately, one may apply a prolonged release coating to reduce the rate of release. A prolonged release coating may also be suitable if one wants to achieve a lag-phase during the first 1 to 2 hours of the in vitro release. As no active is located on the surface of a pharmaceutical composition with a prolonged release coating, no portion of the active can be immediately released as in the case of a prolonged release matrix composition. This leads to an initial lag phase. In order to fine tune the release of an active from a prolonged release coating, one may include pore formers in the coating, e.g. components that are more soluble in water than the prolonged release coating material. Such pore formers will dissolve more quickly than other components and allow for increased penetration of water into the coating and thus release of the actives.

The prolonged release coating may be disposed on individual prolonged release matrix formulations, e.g. beads with a prolonged release matrix, or individual matrix formulations which due to their size despite the use of prolonged release matrix materials do not provide for a prolonged release, e.g. beads with a non-prolonged release matrix, so that a multiparticulate formulation is obtained. These multi-particulates may be directly used, filled into capsules or blended with other excipients to obtain a dosage form such as a tablet, which will instantly disintegrate upon contact with water.

As mentioned above, some preferred aspects and embodiments of the invention include prolonged release multiparticulate pharmaceutical compositions with the single particles comprising the actives hydromorphone and naloxone in a matrix structure made from prolonged release matrix materials such as alkyl celluloses and fatty alcohols. Preferred examples are combinations of ethyl cellulose with a fatty alcohol These particles due to their small size, in certain embodiments, do not provide prolonged release properties. These particles are therefore coated with a prolonged release coating such as an alkylcellulose with ethyl cellulose being preferred. Manufacturing of such prolonged release multiparticulate pharmaceutical compositions is shown in the examples.

For the manufacture of such compositions the actives may be mixed with prolonged release matrix materials, extruded, heat treated and milled to obtain a defined size. The particles are then coated and cured.

Before coating, the particles may be optionally screened in order to select granules of substantially uniform size. Selecting particles of substantially uniform size may improve the prolonged release properties of the final prolonged release pharmaceutical composition. Particles for which at least about 70%, preferably at least about 80%, more preferably at least about 90% are of about the same mean size will typically be considered as being of substantially uniform size.

Preferably, particles are selected of a mean size in the range of about 100 µm to about 5 mm, preferably in the range of about 100 µm to about 4 mm, and more preferably in the range of about 100 µm to about 3 mm. Selection may be performed using a sieve with an appropriate mesh size.

Even though particles may be produced by wet granulation, anhydrous manufacturing steps and methods such as anhydrous extrusion may be preferred. The preference for anhydrous manufacturing steps and methods when making matrix particles is that this has a beneficial impact on the chemical stability of hydromorphone or naloxone or its pharmaceutically acceptable salts. Once the active agents have been included in such a matrix, the additional application of e.g. a prolonged release coating does not have to take place in an anhydrous manner. It is to be understood that the term "anhydrous manufacturing" indicates that the process that leads to e.g. a prolonged release matrix may be performed in the absence of substantial amounts of water. This does not mean that the components which are used do not comprise molecular bound water. Thus, even where the process is performed in an anhydrous manner such as extrusion, naloxone hydrochloride may e.g. be provided as a dihydrate and fillers such as lactose may be provided as lactose monohydrate even though anhydrous lactose can be preferred.

The invention is now illustrated with respect to specific examples. These examples are, however, not to be construed as limiting.

EXAMPLES

I. HMX Ratios for Treating Pain and Improving Opioid-Induced Constipation

Study Design

Methodology and Objectives

This was a randomized, double-Blind, single-dummy, parallel-group, multicentre, 14-week study to establish a hydromorphone prolonged release (PR) to naloxone prolonged release (PR) ratio in subjects taking hydromorphone PR at 8, 24 or 48 mg/day, who had non-cancer or cancer pain that required around-the-clock opioid therapy. The study was composed of two phases: a Pre-randomization Phase (which consisted of the Screening Period and a Run-In Period) and a Maintenance Phase (which consisted of a Double-Blind Phase, an optional Switch-back Phase and a Follow-up Period).

The Pre-randomization Phase was designed to qualify subjects for participation in the Run-In Period. The Run-In Period was designed to titrate hydromorphone PR to analgesic effect (8, 24 or 48 mg/day hydromorphone PR) to be used after randomization, to convert to the study laxative and to qualify subjects for participation in the Double-Blind Phase.

The Double-Blind Phase was designed to establish an optimal hydromorphone PR to naloxone PR dose ratio. For those subjects who completed the 5-week Double-Blind Phase, the optional Switch-back Phase was designed to assess the bowel function and analgesic efficacy in subjects receiving hydromorphone PR alone.

During the adverse events (AE) Follow-up Visit (AE FU) only safety assessment (AE) and assessment of concomitant medication use were conducted. For subjects not entering the Switch-back Phase, this AE FU visit was done 7 days after V10, subjects entering the Switch-back Phase were followed up 7 days after V11.

FIG. 1 presents the study diagram. The run-in period was designed to titrate HM PR (8, 24 or 48 mg/day) to analgesic effect to be used after randomization, to convert to the study laxative and to qualify subjects for participation in the Double-blind Phase. At the start of the Double-blind Phase (Visit 3) subjects were randomized to one of the 4 different ratio groups of HM PR+naloxone PR (2:1, 1:1, 1:2, 1:3) or HM PR+naloxone PR placebo (1:0). For those subjects who completed the 5 week Double-blind Phase, an optional Switch-back Phase with HM PR alone was foreseen to assess the bowel function and analgesic efficacy.

The primary objectives were:
To investigate whether a prolonged release hydromorphone/naloxone combination will lead to comparable analgesia (using numerical range scale (NRS) pain) with a decrease in constipation (Bowel Function Index (BFI)) in patients with moderate to severe chronic non-cancer or cancer pain suffering from constipation caused or aggravated by opioids when compared with hydromorphone alone.
To investigate the optimal dose ratio of hydromorphone and naloxone based on findings of the pain and bowel assessments and safety data.
Secondary objectives included:
To assess the frequency of rescue medication use.
To assess the incidence/frequency of laxative use.
Exploratory objectives included:
To assess bowel function, pain parameters and safety parameters during the Switch-back Phase.

Criteria for Evaluation

Efficacy assessments were collected in daily diaries and during periodic visits. The Primary efficacy variables were the Bowel Function Index (BFI) and the mean average pain over the last 24 hours. Secondary efficacy variables were the rescue medication use, laxative use and CSBMs.

The BFI is described in Rentz et al., *Journal of Medical Economics*, 2009, 12(0):371-383. It is a measure for opioid-induced constipation and has been validated by clinical trials. Bowel Function Index (BFI) is the mean of the following items (assessed at each visit): Ease of defecation (numerical analogue scale [NAS], 0=easy/no difficulty; 100=severe difficulty), Feeling of incomplete bowel evacuation (NAS, 0=not at all, 100=very strong), Personal judgment of constipation (NAS, 0=not at all, 100=very strong).

The 24 hours pain NRS scale is commonly used to evaluate pain in subjects with chronic nonmalignant pain (CPMP/EWP/612/00).

Laxative rescue use could potentially mask treatment differences on constipation relief. To reduce the effect of such masking, a restrictive, standardized laxative regimen, and laxative as rescue medication, was required to minimize the interference with the bowel function endpoints. Therefore, to avoid a masking effect of the laxative intake, only one laxative was provided in a standardized regimen (bisacodyl), that could be used no sooner than 72 hours after a subject's most recent bowel movement (BM) or after randomization. However, if subjects reported discomfort during the described periods they were allowed to take bisacodyl earlier. On the other hand, there was a limit of weekly laxative intake, because of the previously described impact on validity of bowel analysis. Therefore the maximum allowed amount of bisacodyl was not to exceed 5 dosages within 7 consecutive days during the Double-Blind Phase.

The comparator, hydromorphone prolonged release (HM PR), is an opioid that is known to cause constipation. In the study the open combination of HM PR and naloxone matched placebo treatment (in the Double-Blind Phase) served as a placebo comparator with respect to the effect of naloxone on the bowel function.

The safety parameters used in this study included an evaluation of opioid withdrawal by the Modified Subjective Opiate Withdrawal Scale (SOWS). The SOWS consists of 16 items that reflect the common motor, autonomic, gastrointestinal, musculoskeletal, and psychic symptoms of opiate withdrawal. The Modified SOWS excluded the SOWS item number 16, "I feel like shooting up today," since it does not apply to the target subject population.

Safety was assessed using adverse events (AEs, learned through spontaneous reports, subject interview), clinical laboratory results, vital signs, physical examinations, electrocardiograms (ECGs) and modified subjective opioid withdrawal symptoms (SOWS).

Duration of Treatment
Screening Period:
The screening could take up to 14 days. At Visit 1, after written informed consent was obtained, subjects underwent complete evaluation for study eligibility (i.e., all inclusion/exclusion criteria). Subjects who met the Prospective Assessment Criteria continued in the study.
Run-In Period:
The Run-In Period could last up to 28 days. At Visit 2, subjects had their prestudy opioid therapy converted to open-label Hydromorphone (HM) PR, which was titrated to an effective analgesic dose of 8, 24 or 48 mg/day of HM PR at the end of the Run-In Period. Other daily doses than 8, 24 or 48 mg HM PR were allowed for titration only. Hydromorphone immediate-release (HM IR) was available as rescue medication. Subjects also had their pre-study laxative therapy converted to the study laxative to be used per the study routine for constipation during this period. The 7-day baseline assessment in the Run-In Period started no sooner than the day of the initial dose conversion to HM PR. Subjects were contacted on a regular basis (every 2-3 days) to assess pain control and to decide if uptitration of the HM PR dose was necessary.
Maintenance Phase:
The Maintenance Phase included the Double-Blind and Switch Back Phase
Double-Blind Phase:
The Double-Blind Phase was 5 weeks in duration. At Visit 3, subjects who qualified for entry into the Double-Blind Phase of the study were randomized to one of the 4 different ratios of the open combination (non-fixed) of HM PR+naloxone PR or HM PR+naloxone PR placebo in a 1:1:1:1:1 patient number ratio and received study medication for up to 5 weeks (each group consists of 30 subjects). The subject's HM PR dose was the dose the subjects were stabilized on at the end of the Run-In Period (8, 24 or 48 mg HM PR per day). Subjects stabilized on 8 mg HM PR per day at the end of the Run-In Period were switched in a direct way to the respective naloxone dose at the start of the Double-Blind Phase. Subjects stabilized on 24 mg or 48 mg HM PR per day were switched in a stepwise manner to the respective naloxone dose within the first week of the Double-Blind Phase.

TABLE 1

| Hydromorphone dose [per day] | Hydromorphone/Naloxone ratios | | | | |
|---|---|---|---|---|---|
| | 1:0 (Placebo) | 2:1 | 1:1 | 1:2 | 1:3 |
| | Absolute Naloxone dose [mg] per day | | | | |
| 8 mg | 0 | 4 | 8 | 16 | 24 |
| 24 mg | 0 | 12 | 24 | 48 | 72 |
| 48 mg | 0 | 24 | 48 | 96 | 144 |

Hydromorphone immediate release (HM IR) was allowed as rescue medication for the treatment of breakthrough pain. Subjects were only to take a dose of rescue medication if their pain was uncontrolled. Subjects who consistently (i.e. ≥3 days per week) required >2 rescue doses per day were discontinued from the study. Uptitration of the HM PR dose was not allowed during the Double-Blind Phase. Subjects requiring uptitration were discontinued from the study.

If subjects experienced constipation throughout the Double-Blind treatment phase, subjects were given bisacodyl tablets to take as a laxative medication. Bisacodyl tablets were to be used no sooner than 72 h after the subjects' most recent bowel movement (BM). Overall, the maximum allowed amount of bisacodyl was not to exceed 5 dosages bisacodyl 10 mg/day within 7 consecutive days. Following randomization, subjects attended 3 telephone visits (V4, V5 and V6) during the first week of the Double-Blind Phase. There were 4 clinic visits (V7, V8, V9 and V10) at 1 week, 2 weeks, 4 weeks and 5 weeks of the Double-Blind Phase, respectively.

Switch-Back Phase:

At Visit 10, subjects who completed the 5 week Double-Blind Phase had the option to enter a 2 week Switch-back Phase, in which they were switched in a direct manner to open-label HM PR alone. Subjects entering the Switch-back Phase were started on the HM PR dose they were assigned to during the Double-Blind Phase. No dose titration was allowed during the Switch-back Phase.

Subjects were contacted 7 days after the end of the Switch-back Phase for follow up (AE FU) of any ongoing adverse events (AEs) and to record any new AEs that may have occurred.

Number of Subjects 852 subjects were screened and 417 subjects were randomized to the study, of which 346 completed the study. Overall baseline characteristics were similar across all ratio groups. In total, approximately 133 subjects were to be recruited for each dose strength of HM PR (8, 24 or 48 mg HM PR/day). Overall, 80 subjects were to be randomized per HM PR:naloxone ratio. Within each dose strength of HM PR five HM PR:naloxone ratios were used (1:0 (placebo), 2:1, 1:1, 1:2 and 1:3), so that approximately 27 subjects were randomized to each one of these ratios per HM PR dose.

Criteria for Inclusion and Exclusion

Inclusion Criteria:

Subjects included in the study were those who met all of the following criteria:

1. Male or female subjects at least 18 years (females less than one year post-menopausal must have had a negative serum or urine pregnancy test prior to the first dose of study medication, be non-lactating, and willing to use adequate and highly effective methods of contraception throughout the study. A highly effective method of birth control is defined as one which results in a low failure rate (i.e. less than 1% per year) when used consistently and correctly, such as sterilization, implants, injectables, combined oral contraceptives, some IUDs (Intrauterine Device, hormonal), sexual abstinence or vasoectomised partner.

2. Subjects who were receiving WHO step II or step III analgesic medication for the treatment of non-cancer or cancer pain.

3. Subjects with constipation caused or aggravated by opioids:

Subject's medical need of regular intake of laxatives to have at least 3 bowel evacuations per week, or having less than 3 bowel evacuations when not taking a laxative, respectively.

In the opinion of the subject and Investigator it was confirmed that the subject's constipation is induced, or worsened by the subjects pre study opioid medication (present at Screening).

4. Subjects must have been willing to discontinue their current opioid analgesic routine.

5. Subjects must have been willing to discontinue their current laxative regimen and willing to comply with the use of oral bisacodyl as laxative rescue medication.

6. Subjects taking daily fiber supplementation or bulking agents were eligible if they could be maintained on a stable dose and regimen throughout the study, and in the Investigator's opinion were willing and able to maintain adequate hydration.

7. Subjects must have been willing and able (e.g. mental and physical condition) to participate in all aspects of the study, including use of medication, completion of subjective evaluations, attending scheduled clinic visits, completing telephone contacts, and compliance with protocol requirements as evidenced by providing written, informed consent.

8. In the Investigator's opinion, the subject's non-analgesic concomitant medications, including those medications for the treatment of depression were thought to be stable, and would remain stable throughout the Double-Blind Phase of the study.

9. In the Investigator's opinion, the non opioid analgesic medication dose would remain stable during the Double-Blind Phase.

Exclusion Criteria:

Subjects who were excluded from the study were those who met any of the following criteria:

1. Any history of hypersensitivity to hydromorphone, naloxone, bisacodyl, related products or other ingredients of the study medication.

2. Any contraindication to hydromorphone, naloxone, bisacodyl and other ingredients of the study medication.

3. Active alcohol or drug abuse and/or history of opioid abuse.

4. Evidence of clinically significant cardiovascular, renal, hepatic, gastrointestinal (e.g. paralytic ileus), or psychiatric disease, as determined by medical history, clinical laboratory tests, ECG results, and physical examination, that would have placed the subject at risk upon exposure to the study medication or that may have confounded the analysis and/or interpretation of the study results.

5. Chronic or intermittent pain that resulted from Fibromyalgia or Rheumatoid Arthritis.
6. Subjects receiving hypnotics or other central nervous system (CNS) depressants that, in the Investigator's opinion, may have posed a risk of additional CNS depression with opioid study medication.
7. Subjects with uncontrolled seizures or convulsive disorder.
8. Surgery within 2 months prior to the start of the Screening Period, or planned surgery during the 8-week Maintenance Phase that may have affected GI motility or pain.
9. Subjects taking, or who had taken, naloxone ≤30 days prior to the start of the Screening Period.
10. Subjects suffering from diarrhea.
11. Subjects with any situation in which opioids are contraindicated (e.g. severe respiratory depression with hypoxia and/or hypercapnia, severe chronic obstructive lung disease, paralytic ileus).
12. Subjects with hypothyroidism, Addison's disease, increase of intracranial pressure.
13. Abnormal aspartate aminotransferase (AST; SGOT), alanine aminotransferase (ALT; SGPT), or alkaline phosphatase levels (>3 times the upper limit of normal).
14. Abnormal total bilirubin and/or creatinine level(s) (greater than 1.5 times the upper limit of normal), gamma glutamyl transpeptidase (GGT or GGTP) ≥5 times the upper limit of normal.

Other Criteria

Criteria for Entry into the Double-Blind Phase:
1. Subjects continued to satisfy Screening Inclusion/Exclusion criteria.
2. Subject's HM PR dose was 8, 24 or 48 mg/day.
3. Subjects must have rated their pain ("average pain" over the last 24 hours) as ≤4 on 0-10 scale with less than or equal to two doses of hydromorphone immediate release (HM IR) rescue medication per day (Appendix, Section 12.2 for doses of HM IR) for either the last three consecutive days or four of the last seven days.
4. Subjects must have confirmed opioid related constipation, which was defined as having less than 3 CSBM during the last 7 days of the Run-In Period.
5. Subjects demonstrated compliance with laxative use (oral bisacodyl), taking open-label HM PR, and completing daily diaries.

Test Treatment, Dose, and Mode of Administration

Treatments Administered:

Study medication includes any drug(s) under evaluation in the study, including reference drug(s) and placebo but not including rescue medication.

The treatments administered in the study are presented below:

Hydromorphone PR capsules, 4, 8 or 24 mg twice daily

Naloxone PR tablets 2, 8 or 32 mg twice daily

Matched placebo for naloxone PR

Composition of Medications

Hydromorphone PR capsules were provided in the form of Palladone® SR capsules in dosage strengths of 4, 8, and 24 mg.:

Formulation of naloxone PR tablets:

TABLE 2

| | Quantity (mg/tablet) | | | Function |
|---|---|---|---|---|
| Active constituent | | | | |
| Naloxone HCl dihydrate[2] | (2.18) | (8.72) | (34.88) | Active ingredient |
| Corresponds to Naloxone HCl anhydrous[1] | 2 | 8.00 | 32.00 | |
| Other constituents | | | | |
| Hydroxypropyl cellulose[1] | 5.00 | 5.00 | 5.00 | Binder |
| Ethyl cellulose N45[1] | 20.00 | 20.00 | 20.00 | Retardant |
| Stearyl alcohol[1] | 25.00 | 25.00 | 25.00 | Retardant |
| Lactose anhydrous[1] | 77.25 | 71.25 | 47.25 | Diluent |
| Purified talc[1] | 2.50 | 2.50 | 2.50 | Glidant |
| Magnesium stearate[1] | 1.25 | 1.25 | 1.25 | Lubricant |
| Total tablet weight | 133.18 | 133.72 | 135.88 | |

[1]for reference see European Pharmacopeia, 6th edition.
[2]calculated based on assay and moisture content.

The tablets were produced by mixing naloxone HCl with lactose anhydrous, stearyl alcohol, hydroxypropyl cellulose and ethyl cellulose N45 as a prolonged release polymer. Subsequently the blend was melt extruded using a heated twin screw extruder. The extruded strands were milled and the milled granules were blended with magnesium stearate and talc in a tumbler mixer to produce monolithic tablets.

Formulation of Matched Placebo Naloxone PR Tablets:

TABLE 3

| | Quantity (mg/tablet) |
|---|---|
| Hydroxypropyl cellulose[1] | 5.00 |
| Ethyl cellulose N45[1] | 20.00 |
| Stearyl alcohol[1] | 25.00 |
| Lactose anhydrous[1] | 79.25 |
| Purified talc[1] | 2.50 |
| Magnesium stearate[1] | 1.25 |
| Total tablet weight | 133.00 |

[1]for reference see European Pharmacopeia 6th edition.

The tablets were produced as described above for the naloxone tablets.

Run-In Period:

At Visit 2, subjects had their pre-study opioid therapy converted to open-label HM PR, which was titrated to an effective analgesic dose of 8, 24 or 48 mg/day of HM PR at the end of the Run-In Period. Subjects also had their pre-study laxative therapy converted to the study laxative to be used per the study routine for constipation during this period (no sooner than 72 hours after their most recent bowel movement (BM) as rescue medication for constipation).

TABLE 4

| Test Medication | Dosage Form | Unit Strength | Dosing Frequency | Mode of Administration |
|---|---|---|---|---|
| Hydromorphone PR | Capsules | 4, 8, 24 mg hydromorphone | q12h | Oral |

Double-Blind Phase:

Subjects started the Double-Blind Phase at the same dose level (in mg hydromorphone PR/day) that they received at the end of the Run-In Period (8, 24 or 48 mg/day). Subjects stabilized on 4 mg HM PR twice daily at the end of the Run-In Period were switched directly to the respective naloxone dose at the start of the Double-Blind Phase. Subjects stabilized on 12 mg or 24 mg HM PR twice daily were switched in a stepwise manner to the respective naloxone dose within the first week of the Double-Blind Phase. The first dose of Double-Blind study medication was the evening dose of Visit 3. Subjects received Double-Blind study medication for up to 5 weeks. The HM PR dose and the respective naloxone doses are demonstrated in Table 5.

TABLE 5

Total daily dose of naloxone depending on the HM PR:naloxone ratio

| Hydromorphone dose [per day] | Hydromorphone/Naloxone ratios | | | | |
|---|---|---|---|---|---|
| | 1:0 (Placebo) | 2:1 | 1:1 | 1:2 | 1:3 |
| | Absolute Naloxone dose [mg] per day | | | | |
| 8 mg | 0 | 4 | 8 | 16 | 24 |
| 24 mg | 0 | 12 | 24 | 48 | 72 |
| 48 mg | 0 | 24 | 48 | 96 | 144 |

Reference Treatment, Dose, and Mode of Administration

Subjects randomized to the open combination of HM PR and matched placebo for naloxone PR tablets started the Double-Blind Phase with a dose of HM PR established during the Run-In Period (8, 24 or 48 mg HM PR per day) and the respective naloxone placebo dose the subject was randomized to.

TABLE 6

| Test Medication | Dosage Form | Unit Strength | Dosing Frequency | Mode of Administration |
|---|---|---|---|---|
| Hydromorphone PR | Capsules | 4, 8, 24 mg hydromorphone | q12h | Oral |
| Matched placebo for Naloxone PR | Tablet | 2, 8, 32 mg naloxone placebo | q12h | Oral |

Statistical Methods

Statistical programming and analyses were performed using SAS® version 9.2 (SAS Institute, Cary, N.C. 27513).

Populations

Enrolled Population: The enrolled population was defined as all subjects who signed informed consent. Randomized Population: The randomized population was defined as all randomized subjects. Full Analysis Population: The full analysis population was defined as all randomized subjects who received at least one dose of study medication and had at least one post-baseline primary efficacy endpoint, the BFI. Per Protocol Population: The per protocol population was defined as all full analysis population subjects without major protocol violations. Run-in Safety Population: The safety population was defined as all enrolled subjects who received at least one dose of open-label HM PR in the Run-in Period. Double-Blind Safety Population: The safety population was defined as all randomized subjects who received at least one dose of study medication in the Double-Blind Period. Switch-back Safety: Subjects who received at least one dose of open-label HM PR during the Switch-back Phase.

Efficacy Analyses:

An appropriate HMX ratio was defined as:

non-inferior analgesic efficacy compared to the HM plus placebo group, and superior bowel function based on the BFI value compared to the HM plus placebo group BFI and Pain intensity were tested separately. The primary analysis for BFI was based on a comparison of the change from baseline (Visit 3) to end of Double-Blind Phase (week 5) BFI scores between the HM plus placebo group and the various HMX ratio groups. The objective of the analysis of BFI was to show that an HMX ratio is superior to HM plus placebo, using a one-tailed test. The change from baseline (Visit 3) to end of Double-Blind Phase (week 5) in BFI score was analyzed using an Analysis of Covariance (ANCOVA) model with treatment as a fixed-effect factor, baseline (Visit 3) BFI score as a fixed-effect continuous covariate and centre as random-effect factor. The treatment difference, the p-value, the associated 90% confidence interval and the 95% confidence interval were calculated from the Least Squares (LS) means. The result of this analysis was used as a confirmatory analysis, since the purpose of the analysis was to determine efficacy.

The primary analysis for Average Pain over the last 24 hours was based on a comparison of the change from baseline (Visit 3) to end of Double-Blind Phase (Week 5) scores between the placebo and HMX treatment groups. The change from baseline in Average Pain over the last 24 hours was analyzed using an ANCOVA model on log-transformed data with treatment as a fixed-effect factor, baseline (Visit 3) Average Pain over the last 24 hours as a fixed-effect continuous covariate and centre as random-effect factor. The Averaged Pain Over the Last 24 Hours in the Placebo group was multiplied by 0.8 and log-transformed. The treatment ratio, the p-value, the associated 90% confidence interval and the 95% confidence interval were then calculated from the antilog of the LS means for the treatment difference.

Secondary efficacy analyses included rescue medication intake and laxative use.

Adverse events (AEs) were classified into standardized medical terminology from the verbatim description (Investigator term) using MedDRA (version 14.1).

Opioid withdrawal AEs were defined as AEs with a preferred term "Drug Withdrawal Syndrome". Opioid withdrawal AEs were summarized for each treatment group (ratio, hydromorphone dose and naloxone dose) and overall for the double blind period. Subjects with opioid withdrawal AEs were listed.

Results

1. Demographic and Baseline Characteristics

Overall baseline characteristics were similar across all ratio groups. The distribution of age, gender, race and weight across the ratio groups is shown in Table 7 In total 255 (61.3%) female and 161 (38.7%) male subjects were included, a typical gender distribution in chronic pain studies.

TABLE 7

Demographic and baseline characteristics - Double-blind Safety Population)

| Characteristic | 1:0 (N = 85) | 2:1 (N = 89) | 1:1 (N = 90) | 1:2 (N = 78) | 1:3 (N = 74) | Total (N = 416) |
|---|---|---|---|---|---|---|
| Age (years), mean (SD) | 56.3 (11.70) | 59.6 (11.27) | 57.9 (10.96) | 59.3 (13.30) | 55.2 (11.74) | 57.7 (11.84) |
| Gender | | | | | | |
| Female, n (%) | 49 (57.6) | 54 (60.7) | 49 (54.4) | 53 (67.9) | 50 (67.6) | 255 (61.3) |
| Male, n (%) | 36 (42.4) | 35 (39.3) | 41 (45.6) | 25 (32.1) | 24 (32.4) | 161 (38.7) |
| Race | | | | | | |
| Caucasian, n (%) | 81 (95.3) | 86 (96.6) | 83 (92.2) | 76 (97.4) | 72 (97.3) | 398 (95.7) |
| Black, n (%) | 4 (4.7) | 3 (3.4) | 7 (7.8) | 1 (1.3) | 2 (2.7) | 17 (4.1) |
| Other, n (%) | 0 (0.0) | 0 (0.0) | 0 (0.0) | 1 (1.3) | 0 (0.0) | 1 (0.2) |
| Weight (kg), mean (SD) | 86.7 (22.01) | 88.1 (21.87) | 88.4 (23.61) | 85.2 (19.19) | 87.6 (20.82) | 87.3 (21.57) |

2. Disposition/Exposure

In total 417 subjects were randomized. One subject discontinued prior to first dose leading to a Double-blind safety population of 416 subjects. 406 subjects were included in the Full-Analysis population and 319 subjects in the Per-protocol population.

Overall approx. 80% of the subjects completed the study. The completion rate was comparable across the different treatment groups with the highest number in the 1:0 ratio (75 subjects (88.2%)) and the lowest number in the 2:1 ratio (70 subjects (78.7%)). The number of subjects discontinuing prematurely from the study was generally low. The most frequent reason for premature discontinuation in all treatment groups was the experience of AEs (see Table 8).

ent differences in the intensity of mean pain between any treatment groups were observed during the 5 weeks Double-blind Phase (see Table 9). Mean pain scores remained low and stable throughout the entire Double-blind Phase indicating that the combination of hydromorphone and naloxone have a similar analgesic efficacy compared to the single entity hydromorphone and that the naloxone component does not have any influence on the analgesic efficacy.

Non-inferiority of all hydromorphone/naloxone treatment groups to the hydromorphone/placebo treatment was demonstrated by the primary statistical analysis in change from baseline to week 5, as confirmed by statistically significant p-values (test for non-inferiority) for all naloxone groups

TABLE 8

Summary of Disposition - Double-blind Safety Population

| | Hydromorphone:Naloxone Dose Ratio | | | | | |
|---|---|---|---|---|---|---|
| | 1:0 (N = 85) | 2:1 (N = 89) | 1:1 (N = 90) | 1:2 (N = 78) | 1:3 (N = 74) | Total (N = 416) |
| Subjects completed | 75 (88.2) | 70 (78.7) | 75 (83.3) | 65 (83.3) | 61 (82.4) | 346 (83.2) |
| Subjects discontinued | 10 (11.8) | 19 (21.3) | 15 (16.7) | 13 (16.7) | 13 (17.6) | 70 (16.8) |
| Primary reason for discontinuation: | | | | | | |
| Adverse Events(s) | 4 (4.7) | 7 (7.9) | 11 (12.2) | 6 (7.7) | 6 (8.1) | 34 (8.2) |
| Subjects choice | 1 (1.2) | 5 (5.6) | 1 (1.1) | 1 (1.3) | 1 (1.4) | 9 (2.2) |
| Lost to follow-up | — | — | 1 (1.1) | — | — | 1 (0.2) |
| Administrative | 3 (3.5) | 3 (3.4) | 1 (1.1) | 4 (5.1) | 3 (4.1) | 14 (3.4) |
| Lack of therapeutic effect | 2 (2.4) | 4 (4.5) | 1 (1.1) | 2 (2.6) | 3 (4.1) | 12 (2.9) |

3. Efficacy Parameters
3.1 Analgesic Efficacy Parameters
3.1.1 Average 24 Hours Pain At baseline (randomization) the mean pain scores (average 24 hours pain) were comparable in all treatment groups. In the primary analysis population (Per-protocol) no appar- (2:1 ratio: p=0.005, 1:1 ratio: p<0.001, 1:2 ratio: p=0.002 and 1:3 ratio: p<0.001). Results of the statistical analysis are shown in Table 10.

There was no major change in mean pain intensity in any of the treatment groups from the end of the Double-blind Phase to the end of the Switch-back Phase, when patients were receiving hydromorphone alone.

TABLE 9

Primary Statistical Analysis of the Change from Baseline to Week 5 in Average Pain (LOCF) by Hydromorphone/Naloxone Ratio (PP Population)

| Statistic | Hydromorphone Naloxone 1:0 Ratio (N = 73) | Hydromorphone Naloxone 2:1 Ratio (N = 61) | Hydromorphone Naloxone 1:1 Ratio (N = 66) | Hydromorphone Naloxone 1:2 Ratio (N = 60) | Hydromorphone Naloxone 1:3 Ratio (N = 59) |
|---|---|---|---|---|---|
| n | 73 | 61 | 66 | 60 | 59 |
| LSMean | 105.77 | 97.43 | 102.61 | 99.19 | 111.22 |
| 95% CI | (98.45, 113.64) | (90.08, 105.38) | (95.16, 110.65) | (91.63, 107.37) | (102.69, 120.46) |
| LSMean Difference | | 92.12 | 97.02 | 93.78 | 105.15 |
| 90% CI | | (84.26, 100.70) | (88.90, 105.87) | (85.73, 102.58) | (96.11, 115.05) |
| 95% CI | | (82.83, 102.45) | (87.42, 107.66) | (84.26, 104.37) | (94.46, 117.06) |
| P-Value | | 0.005 | p < 0.001 | 0.002 | p < 0.001 |

N: Number of subjects in population,
n: Number of subjects with data available.
The change in Pain score using Last Observation Carried Forward (LOCF) was analyzed using an Analysis of Covariance (ANCOVA) model with treatment (fixed) and centre (random) as factors and baseline Pain score (fixed) as a covariate.
Natural log parameter estimates calculated by transforming the log-scale estimates back to the linear scale, that is estimates of ratios.
Confidences intervals obtained by transforming the confidence intervals on the log-scale to the ratio scale.
P-Value calculated using a 0.8 adjustment on reference ratio 1:0.

TABLE 10

Statistical Analysis of the Change from Baseline to Week 5 in Average Pain by Hydromorphone/Naloxone Ratio (PP Population)

| Statistic | Hydromorphone Naloxone 1:0 Ratio (N = 73) | Hydromorphone Naloxone 2:1 Ratio (N = 61) | Hydromorphone Naloxone 1:1 Ratio (N = 66) | Hydromorphone Naloxone 1:2 Ratio (N = 60) | Hydromorphone Naloxone 1:3 Ratio (N = 59) |
|---|---|---|---|---|---|
| n | 66 | 56 | 62 | 56 | 53 |
| LSMean | 102.20 | 94.36 | 100.73 | 99.17 | 109.40 |
| 95% CI | (95.07, 109.88) | (87.24, 102.06) | (93.49, 108.53) | (91.66, 107.30) | (100.93, 118.59) |
| LSMean Difference | | 92.32 | 98.56 | 97.03 | 107.04 |
| 90% CI | | (84.42, 100.96) | (90.33, 107.53) | (88.69, 106.16) | (97.75, 117.22) |
| 95% CI | | (82.98, 102.72) | (88.83, 109.35) | (87.17, 108.02) | (96.06, 119.29) |
| P-Value | | 0.004 | p < 0.001 | p < 0.001 | p < 0.001 |

3.1.2 Analgesic Rescue Medication

Overall the analgesic rescue medication intake was low and comparable across all treatment groups, demonstrating that the naloxone component did not have any effect on the analgesic efficacy of hydromorphone (see Table 11).

TABLE 11

Summary of Rescue Medication Use - Full Analysis Population

| | | Hydromorphone:Naloxone Dose Ratio | | | | | |
|---|---|---|---|---|---|---|---|
| | Statistic | 1:0 (N = 85) | 2:1 (N = 82) | 1:1 (N = 80) | 1:2 (N = 81) | 1:3 (N = 78) | Total (N = 406) |
| Averaged Number of Intakes per Day | N | 85 | 82 | 80 | 81 | 78 | 406 |
| | Mean | 0.73 | 0.58 | 0.73 | 0.65 | 0.80 | 0.70 |
| | (SD) | (0.740) | (0.700) | (0.807) | (0.716) | (0.806) | (0.754) |
| | Median | 0.47 | 0.28 | 0.35 | 0.40 | 0.50 | 0.38 |
| | Min, Max | 0.0, 2.6 | 0.0, 2.3 | 0.0, 3.2 | 0.0, 3.4 | 0.0, 2.5 | 0.0, 3.4 |

3.2. Bowel Function Parameters 3.2.1 Bowel Function Index (BFI)

The results of the BFI are presented as descriptive statistics as well as confirmatory statistics. The BFI score is compiled from the responses to three questions about ease of defecation, feeling of incomplete bowel movement and the subject's personal judgment of constipation.

Figure 2:
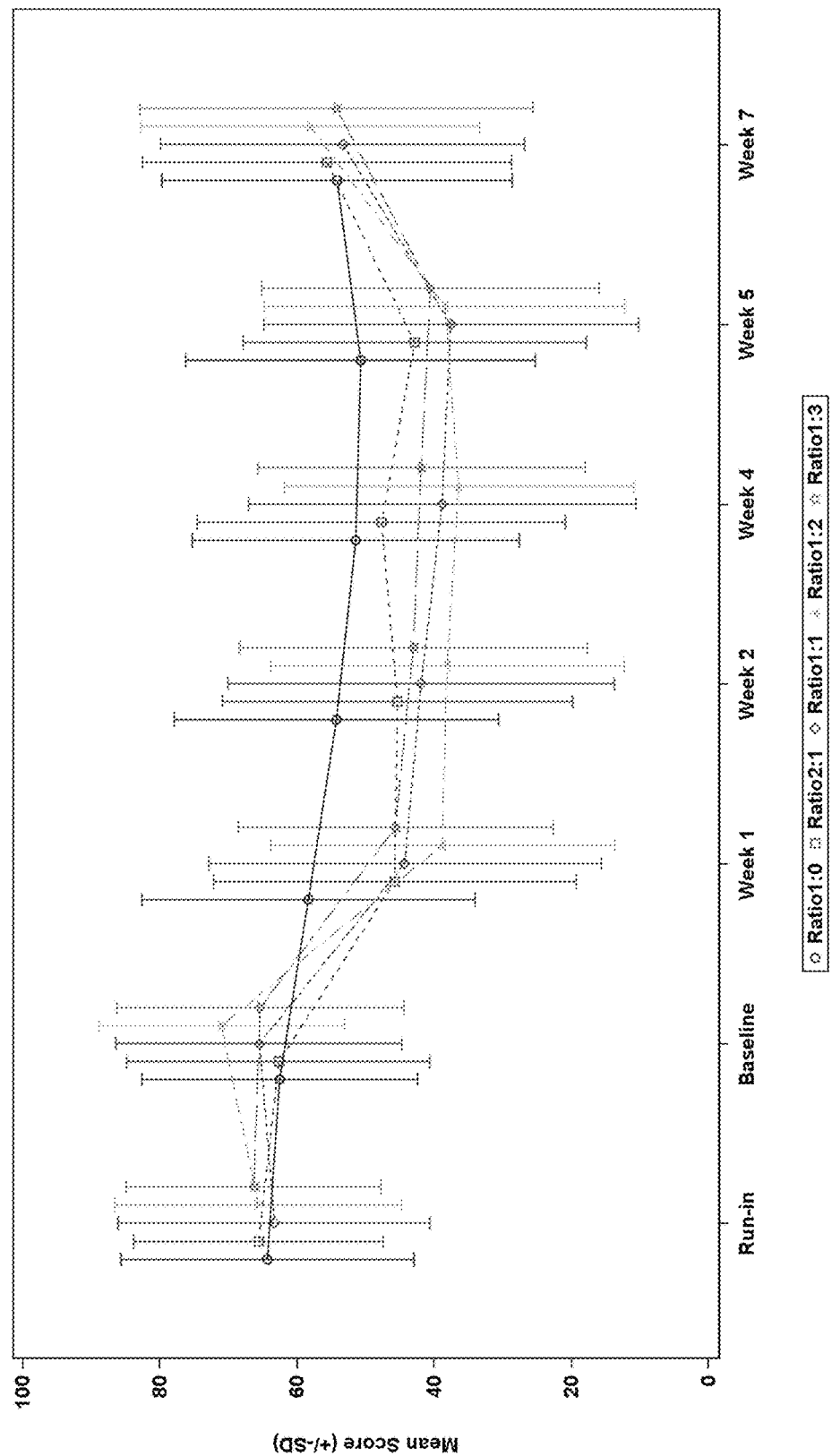
FIG. 2 shows Bowel Function Index (BFI) (observed values) by hydromorphone/naloxone ratio—Full Analysis Population.

At baseline (randomization) mean BFI values were high and comparable across all treatment groups. By the end of the Double-blind Phase all treatment groups receiving naloxone had a clinically relevant improvement in mean BFI values, whereas in the hydromorphone/naloxone placebo treatment group a clinically relevant improvement in mean BFI scores was not observed. Observed BFI values for the Full Analysis population are described in FIG. 2.

The removal of naloxone from the treatment regimen during the Switch-back Phase resulted in an increase in mean BFI values, indicating a worsening of bowel function. At the end of the Switch-back Phase, mean BFI values had almost returned to baseline values (see FIG. 2).

A clinically relevant improvement in BFI values was seen in all hydromorphone/naloxone treatment groups (2:1 ratio: −20.33; 1:1 ratio: −26.71; 1:2 ratio: −28.94 and 1:3 ratio: −23.61, compared to −14.15 with the 1:0 ratio placebo treatment group) (Table 12). When the placebo result is taken into account it can be seen that the clinical relevance of the BFI improvement remains with the 1:1 and 1:2 ratios but is borderline with the 1:3 ratio (−15.02, 17.25 and −11.92 respectively).

The results shown in Table 13 confirm that the change in BFI score from baseline to Week 5 was statistically relevant for all hydromorphone/naloxone ratios and clinically relevant for the 1:1 and 1:2 ratios. The LS mean differences (SE) in Table 12 and Table 13 are based on the ANCOVA model, adjusted by the change in mean BFI value in the naloxone placebo treatment group (1:0 ratio group)

3.2.2 Rescue Laxative

Because of the potential for laxatives complicating the primary analysis, a restrictive laxative regimen was applied, as defined in the study protocol.

Overall the average number of rescue laxative taken was low with a slightly higher intake per day in the 1:0 ratio treatment group (naloxone placebo group) compared to all other treatment groups receiving naloxone. This finding is concordant with the results of BFI showing that improvement in bowel function was not influenced by the laxative intake and the benefit was solely attributed to the combination of hydromorphone and naloxone (see Table 14).

TABLE 12

Primary Statistical Analysis of the Change from Baseline to Week 5 in BFI - LOCF by Hydromorphone/Naloxone Ratio: FA population

| Statistic | Hydromorphone/Naloxone Ratio | | | | |
|---|---|---|---|---|---|
| | 1:0 (N = 85) | 2:1 (N = 82) | 1:1 (N = 80) | 1:2 (N = 81) | 1:3 (N = 78) |
| n | 85 | 82 | 80 | 81 | 78 |
| LSMean | −11.69 | −20.33 | −26.71 | −28.94 | −23.61 |
| 95% CI | (−17.07, −6.31) | (−25.81, −14.85) | (−32.25, −21.17) | (−34.49, −23.40) | (−29.22, −18.00) |
| LSMean Difference (SE) | | −8.64 (3.90) | −15.02 (3.93) | −17.25 (3.95) | −11.92 (3.95) |
| 90% CI | | (−15.07, −2.22) | (−21.50, −8.54) | (−23.76, −10.75) | (−18.44, −5.40) |
| 95% CI | | (−16.31, −0.98) | (−22.74, −7.30) | (−25.01, −9.50) | (−19.69, −4.15) |
| P-Value | | 0.014 | p < 0.001 | p < 0.001 | 0.001 |

N: Number of subjects in population, n: Number of subjects with data available.

The change in BFI score using LOCF was analyzed using an ANOVA model with treatment (fixed) and centre (random) as factors and baseline BFI score (fixed) as a covariate.

TABLE 13

Statistical Analysis of the Change from Baseline to Week 5 in BFI by Hydromorphone/Naloxone Ratio: FA population

| Statistic | Hydromorphone/Naloxone Ratio | | | | |
|---|---|---|---|---|---|
| | 1:0 (N = 85) | 2:1 (N = 82) | 1:1 (N = 80) | 1:2 (N = 81) | 1:3 (N = 78) |
| N | 75 | 67 | 72 | 66 | 60 |
| LSMean | −14.15 | −22.36 | −28.24 | −29.35 | −25.66 |
| 95% CI | (−19.77, −8.54) | (−28.29, −16.43) | (−33.95, −22.52) | (−35.35, −23.34) | (−31.92, −19.40) |
| LSMean Difference (SE) | | −8.20 (4.15) | −14.08 (4.07) | −15.19 (4.19) | −11.51 (4.28) |
| 90% CI | | (−15.04, −1.36) | (−20.80, −7.37) | (−22.11, −8.28) | (−18.56, −4.45) |
| 95% CI | | (−16.36, −0.05) | (−22.09, −6.07) | (−23.44, −6.95) | (−19.92, −3.09) |
| P-Value | | 0.024 | p < 0.001 | p < 0.001 | 0.004 |

N: Number of subjects in population, n: Number of subjects with data available.

The change in Bowel Function Index score was analyzed using an Analysis of Covariance (ANCOVA) model with treatment (fixed) and centre (random) as factors and baseline BFI score (fixed) as a covariate.

TABLE 14

Summary of Laxative Use - Averaged Number Intakes per Day by hydromorphone/naloxone ratio - Full Analysis population

| | | Hydromorphone:Naloxone Dose Ratio | | | | | |
|---|---|---|---|---|---|---|---|
| | Statistic | 1:0 (N = 85) | 2:1 (N = 82) | 1:1 (N = 80) | 1:2 (N = 81) | 1:3 (N = 78) | Total (N = 406) |
| Averaged Number Intakes per Day | n | 85 | 82 | 80 | 81 | 78 | 406 |
| | Mean (SD) | 0.15 (0.233) | 0.11 (0.204) | 0.08 (0.153) | 0.09 (0.149) | 0.07 (0.117) | 0.10 (0.179) |
| | Median | 0.04 | 0.03 | 0.03 | 0.03 | 0.00 | 0.03 |
| | Min, Max | 0.0, 1.1 | 0.0, 1.5 | 0.0, 0.8 | 0.0, 0.9 | 0.0, 0.5 | 0.0, 1.5 |

3.3 Subgroup Evaluation of Mean BFI and Mean Pain During Double-Blind and Switch-Back Periods In order to get conclusive evidence on an optimal ratio, a more detailed analysis of the 1:1 and 1:2 ratio was performed, by absolute daily hydromorphone dose with respect to improvement in bowel function, supported by a corresponding analysis on analgesic efficacy.

A subgroup evaluation was performed analyzing the mean BFI (see Table 15) and mean pain (see Table 16) values throughout the Double-Blind and Switch-back Phase, applying the descriptive statistics used for the primary analysis.

TABLE 15

Bowel Function Index - LOCF by Hydromorphone/Naloxone Ratio and Hydromorphone dose - FA Population

| Ratio Group | Baseline mean (SD) | End of Double-blind mean (SD) | Δ BFI mean (SD) | End of Switch Back mean (SD) |
|---|---|---|---|---|
| Hydromorphone 8 mg/day | | | | |
| 1:0 (N = 27) | 57.53 (17.06) | 48.84 (26.83) | −8.69 (23.55) | 49.29 (27.57) |
| 1:1 (N = 24) | 64.24 (19.61) | 38.31 (28.28) | −25.93 (25.27) | 53.47 (28.29) |
| 1:2 (N = 24) | 64.58 (14.18) | 36.67 (22.52) | −27.92 (23.64) | 52.89 (23.31) |
| Hydromorphone 24 mg/day | | | | |
| 1:0 (N = 38) | 65.48 (18.43) | 57.06 (23.76) | −8.42 (25.55) | 59.09 (21.74) |
| 1:1 (N = 38) | 67.28 (21.69) | 38.93 (27.98) | −28.35 (23.46) | 54.84 (25.82) |
| 1:2 (N = 38) | 72.72 (19.38) | 39.47 (27.22) | −33.25 (27.22) | 55.67 (26.32) |
| Hydromorphone 48 mg/day | | | | |
| 1:0 (N = 20) | 63.78 (26.04) | 49.17 (28.12) | −14.62 (28.75) | 51.38 (29.20) |
| 1:1 (N = 18) | 63.70 (21.52) | 39.04 (30.47) | −24.67 (35.67) | 49.58 (26.49) |
| 1:2 (N = 19) | 75.83 (17.63) | 39.70 (30.69) | −35.93 (35.67) | 72.12 (19.79) |

TABLE 16

Mean Pain Score - LOCF by hydromorphone/naloxone ratio and hydromorphone dose - PP population

| Ratio Group | Baseline Mean (SD) | End of Double-blind (Week 5) Mean (SD) | End of Switch Back Mean (SD) |
|---|---|---|---|
| Hydromorphone 8 mg/day | | | |
| 1:0 (N = 22) | 3.3 (0.83) | 3.3 (1.52) | 3.3 (1.19) |
| 1:1 (N = 20) | 3.0 (0.94) | 2.9 (1.33) | 2.9 (1.37) |
| 1:2 (N = 20) | 2.8 (1.29) | 2.6 (1.39) | 3.0 (1.77) |
| Hydromorphone 24 mg/day | | | |
| 1:0 (N = 33) | 3.2 (0.88) | 3.7 (1.38) | 3.8 (1.18) |
| 1:1 (N = 31) | 3.1 (1.08) | 3.3 (1.34) | 3.2 (1.37) |
| 1:2 (N = 27) | 3.4 (1.08) | 3.4 (1.31) | 3.2 (1.33) |
| Hydromorphone 48 mg/day | | | |
| 1:0 (N = 18) | 3.3 (1.02) | 3.9 (1.81) | 3.7 (1.40) |
| 1:1 (N = 15) | 3.5 (1.13) | 4.3 (1.71) | 3.7 (1.25) |
| 1:2 (N = 13) | 3.2 (1.41) | 3.6 (1.12) | 4.8 (1.48) |

At baseline (randomization), mean BFI values were high and comparable in all hydromorphone dose groups and across all ratios (1:0, 1:1, 1:2). In the 8 mg hydromorphone dose group as well as in the 24 mg and 48 mg dose group, both the 1:1 and 1:2 ratios had a clinically relevant improvement in mean BFI values by the end of the Double-Blind Phase (see Table 15.). The evaluation of BFI adjusted by the change in mean BFI value in the naloxone placebo treatment group demonstrated a clinically relevant improvement in bowel function in the 8 mg and 24 mg hydromorphone dose groups for both 1:1 and 1:2 ratios.

However, in the 48 mg hydromorphone dose group the 1:2 ratio showed a marked clinically relevant improvement in bowel function. The results of the 1:1 ratio indicated a borderline clinically relevant improvement. All hydromorphone doses across both ratios demonstrated a high and continuous analgesic efficacy, which was equivalent to the hydromorphone single entity.

3.4 Bowel Function and Pain Parameters in the Switch-Back Phase

During the switchback phase the bowel function started to deteriorate to previous levels and the level of analgesic control remained the same. These findings demonstrate that the addition of naloxone reduces the detrimental effect of hydromorphone on bowel function and also that the addition of naloxone has no effect on the central analgesic effect of hydromorphone 3.5 Efficacy Discussion and Conclusions Irrespective of the ratio between hydromorphone and naloxone, pain scores did not significantly deteriorate during the treatment period but remained unchanged in all treatment groups. Non-inferiority of all hydromorphone/naloxone ratios compared to the hydromorphone/placebo treatment was demonstrated by the statistical analysis, and pain values remained stable until the end of the Switch-back Phase. This was achieved with a very low amount of rescue medication intake in all treatment groups. Based on these results, all hydromorphone/naloxone ratios demonstrated a high and continuous analgesic efficacy, being equivalent to the hydromorphone single entity.

Descriptive statistics showed that all hydromorphone/naloxone ratios except for the hydromorphone/placebo group had a clinically relevant improvement in bowel function compared to baseline, as determined by the BFI values. This was further supported by the statistical analysis of LSMean using the ANCOVA model. Accounting for the LSMean difference analysis as adjusted by the hydromorphone/placebo results, all hydromorphone/naloxone ratio groups showed a statistically significant improvement in bowel function, whilst a marked and clinically relevant improvement was demonstrated in the 1:1 and 1:2 ratio groups, with the highest improvement in the 1:2 ratio group. A less dramatic improvement was observed in the 1:3 ratio group, wherein the improvement was statistically significant compared to the placebo group, but the mean difference was 11.92 and therefore was just below the pre-set clinical goal of 12 points achieved by the 1:1 and 1:2 ratio groups.

A subgroup evaluation was performed, analyzing the mean BFI and mean pain values throughout the Double-Blind and Switch-back Phase and applying the descriptive statistics used for the primary analysis. This concluded that the 1:2 ratio would be well-suited based on its BFI and analgesic efficacy across the entire hydromorphone dose range (Table 15; Table 16.).

Overall, and based on the restricted laxative regimen as defined in the protocol, the average number of rescue laxative intakes was low, demonstrating that improvement in bowel function was not influenced by the laxative intake and could be attributed to the naloxone component. This is further evidenced by the increase in mean BFI values during the Switch-back Phase, during which subjects did not receive naloxone.

6. Safety Analysis 6.1 Adverse Events

In general the incidence of AEs and related AEs was comparable across all treatment groups. In the Double-Blind Safety Population 170 (40.9%) subjects experienced related AEs, which is as expected for this class of drugs and is comparable with that seen in other opioid studies. The percentage of subjects with at least one related AE was also fairly comparable across groups. The number of subjects with severe related AEs was low (5.5% overall), as was the number subjects with related SAEs (0.5%) and SAEs overall (1.0%).

Nausea (32 subjects in total (7.7%)), diarrhea (22 subjects in total (5.3%)), and abdominal pain (20 subjects in total (4.8%)), were the most frequently reported AEs and are consistent with the expected AE profile of the class of drugs used in this study (see Table 17).

TABLE 17

Most Frequent Adverse Events ≥5% of Subjects in Any Treatment Group: Double-Blind Safety Population

| System Organ Class Preferred Term | Hydromorphone:Naloxone Dose Ratio | | | | | |
|---|---|---|---|---|---|---|
| | 1:0 (N = 85), n (%) | 2:1 (N = 89), n (%) | 1:1 (N = 90), n (%) | 1:2 (N = 78), n (%) | 1:3 (N = 74), n (%) | Total (N = 416), n (%) |
| Subjects with at least one AE | 60 (70.6) | 59 (66.3) | 64 (71.1) | 43 (55.1) | 51 (68.9) | 277 (66.6) |
| GASTROINTESTINAL DISORDERS | 22 (25.9) | 26 (29.2) | 24 (26.7) | 14 (17.9) | 21 (28.4) | 107 (25.7) |
| Abdominal pain | 5 (5.9) | 1 (1.1) | 4 (4.4) | 4 (5.1) | 6 (8.1) | 20 (4.8) |
| Abdominal pain upper | 2 (2.4) | 5 (5.6) | 4 (4.4) | 1 (1.3) | 1 (1.4) | 13 (3.1) |
| Diarrhea | 1 (1.2) | 5 (5.6) | 6 (6.7) | 5 (6.4) | 5 (6.8) | 22 (5.3) |
| Nausea | 6 (7.1) | 11 (12.4) | 4 (4.4) | 4 (5.1) | 7 (9.5) | 32 (7.7) |
| Vomiting | 2 (2.4) | 2 (2.2) | 4 (4.4) | 2 (2.6) | 5 (6.8) | 15 (3.6) |
| GENERAL DISORDERS AND ADMINISTRATION SITE CONDITIONS | 6 (7.1) | 12 (13.5) | 11 (12.2) | 8 (10.3) | 11 (14.9) | 48 (11.5) |
| Drug withdrawal syndrome | — | 5 (5.6) | 7 (7.8) | 3 (3.8) | 2 (2.7) | 17 (4.1) |
| INFECTIONS AND INFESTATIONS | 10 (11.8) | 7 (7.9) | 8 (8.9) | 8 (10.3) | 14 (18.9) | 47 (11.3) |
| Nasopharyngitis | — | — | 1 (1.1) | — | 4 (5.4) | 5 (1.2) |
| INVESTIGATIONS | 16 (18.8) | 21 (23.6) | 20 (22.2) | 17 (21.8) | 18 (24.3) | 92 (22.1) |
| Blood uric acid increased | 1 (1.2) | 3 (3.4) | 7 (7.8) | 1 (1.3) | 1 (1.4) | 13 (3.1) |

TABLE 17-continued

Most Frequent Adverse Events ≥5% of Subjects in Any
Treatment Group: Double-Blind Safety Population

| | Hydromorphone:Naloxone Dose Ratio | | | | | |
|---|---|---|---|---|---|---|
| System Organ Class<br>Preferred Term | 1:0<br>(N = 85),<br>n (%) | 2:1<br>(N = 89),<br>n (%) | 1:1<br>(N = 90), n<br>(%) | 1:2<br>(N = 78), n<br>(%) | 1:3<br>(N = 74),<br>n (%) | Total<br>(N = 416),<br>n (%) |
| METABOLISM AND NUTRITION DISORDERS | 3 (3.5) | 6 (6.7) | 3 (3.3) | 3 (3.8) | 4 (5.4) | 19 (4.6) |
| MUSCULOSKELETAL AND CONNECTIVE TISSUE DISORDERS | 11 (12.9) | 10 (11.2) | 13 (14.4) | 1 (1.3) | 11 (14.9) | 46 (11.1) |
| NERVOUS SYSTEM DISORDERS | 10 (11.8) | 11 (12.4) | 8 (8.9) | 7 (9.0) | 5 (6.8) | 41 (9.9) |
| Headache | 2 (2.4) | 7 (7.9) | 6 (6.7) | 1 (1.3) | 2 (2.7) | 18 (4.3) |
| PSYCHIATRIC DISORDERS | 4 (4.7) | 6 (6.7) | 4 (4.4) | 3 (3.8) | 7 (9.5) | 24 (5.8) |
| RESPIRATORY, THORACIC AND MEDIASTINAL DISORDERS | 3 (3.5) | 2 (2.2) | 2 (2.2) | 3 (3.8) | 7 (9.5) | 17 (4.1) |
| SKIN AND SUBCUTANEOUS TISSUE DISORDERS | 5 (5.9) | 5 (5.6) | 4 (4.4) | 6 (7.7) | 6 (8.1) | 26 (6.3) |
| Hyperhidrosis | 3 (3.5) | 3 (3.4) | 4 (4.4) | 5 (6.4) | 3 (4.1) | 18 (4.3) |
| VASCULAR DISORDERS | 1 (1.2) | 6 (6.7) | 2 (2.2) | 4 (5.1) | — | 13 (3.1) |

6.2 Other Observations Related to Safety-Subjective Opioid Withdrawal Scale (SOWS)

At baseline the mean SOWS score in the Double-Blind Safety Population was 7.7 (SD 7.19) and comparably low across treatment groups. These values were stable during the first week of the Double-Blind Phase, where subjects were switched to the complete naloxone dose and remained unchanged until the end of the Double-Blind Phase. This confirmed that the addition of naloxone was not causing any unwanted opioid withdrawal effects.

TABLE 18

Total SOWS Score by Hydromorphone/Naloxone Ratio: Double-Blind Safety Population

| | | Hydromorphone:Naloxone Dose Ratio | | | | | |
|---|---|---|---|---|---|---|---|
| Visit | Statistic | 1:0<br>(N = 85) | 2:1<br>(N = 89) | 1:1<br>(N = 90) | 1:2<br>(N = 78) | 1:3<br>(N = 74) | Total<br>(N = 416) |
| Baseline | n | 85 | 89 | 90 | 78 | 74 | 416 |
| | Mean (SD) | 7.6 (7.38) | 7.4 (7.48) | 7.2 (6.68) | 7.3 (7.19) | 9.1 (7.22) | 7.7 (7.19) |
| | Median | 5.0 | 5.0 | 5.5 | 5.0 | 8.0 | 6.0 |
| | Min, Max | 0, 32 | 0, 37 | 0, 34 | 0, 33 | 0, 35 | 0, 37 |
| Week 1 | n | 80 | 81 | 83 | 70 | 67 | 381 |
| | Mean (SD) | 6.2 (6.93) | 6.5 (7.15) | 6.5 (6.50) | 7.4 (8.81) | 7.4 (6.19) | 6.7 (7.13) |
| | Median | 4.0 | 4.0 | 5.0 | 5.0 | 5.0 | 5.0 |
| | Min, Max | 0, 42 | 0, 36 | 0, 30 | 0, 43 | 0, 28 | 0, 43 |
| Week 5 | n | 72 | 70 | 72 | 63 | 61 | 338 |
| | Mean (SD) | 7.9 (8.31) | 6.6 (5.86) | 6.5 (5.80) | 6.1 (5.72) | 6.9 (5.31) | 6.8 (6.33) |
| | Median | 5.0 | 4.0 | 5.0 | 4.0 | 6.0 | 5.0 |
| | Min, Max | 0, 41 | 0, 21 | 0, 33 | 0, 25 | 0, 19 | 0, 41 |

N: Number of subjects in population,
n: Number of subjects with data available.
Baseline visit is defined as Visit 3.

6.3 Safety Discussion and Conclusions

In total, 277 subjects (66.6%) experienced at least one AE during the Double-Blind phase. There were 623 individual AEs. 170 subjects (40.9%) experienced 324 AEs that were considered by the investigator to be related to study medication.

The most common AEs were: nausea (32 subjects in total (7.7%), diarrhea (22 subjects in total (5.3%), abdominal pain (20 subjects in total (4.8%) and vomiting (15 subjects (3.6%). These are consistent with the expected AE profile of the class of drugs used in this study. The incidence of related GI AEs was equally distributed between the groups.

The incidence of diarrhea was not affected by the ratio of naloxone in the combination.

17 subjects (4.1%) reported an AE of "drug withdrawal syndrome" with a causal relationship to study medication. Incidence rates varied within the ratio and dose groups between 0 and 11.8%, with an overall rate of 4.1%. There was no trend for higher rates of drug withdrawal syndrome in the subgroups with higher naloxone dose or ratio.

The majority of AEs were mild or moderate.

The incidence of AEs considered by the investigator to be related to study medication was similar between the dose ratios.

Haematology, blood chemistry, urinalysis and laboratory values showed no notable differences between the treatment groups.

7. Conclusions

This was a confirmatory study conducted to establish an optimal hydromorphone/naloxone ratio with a comparable analgesic efficacy and improved bowel function compared to hydromorphone based on pain and bowel function assessments as well as safety parameters. According to the patient's pain assessment and the analgesic rescue medication intake, all treatment groups demonstrated the same analgesic efficacy. Therefore, regarding the analgesic efficacy of hydromorphone/naloxone, all ratios can be considered suitable for a fixed combination product. The most frequently reported AEs were consistent with the expected AE profile of the opioid analgesic class of drugs.

There were no new or unexpected AEs observed which were attributable to the administration of hydromorphone/placebo or hydromorphone/naloxone treatment groups. Therefore, the safety profile was consistent with those of other strong opioids. SOWS sum scores were low and stable, indicating that whilst occasional single susceptible patients may be affected by withdrawal syndrome after the addition of naloxone, it does not appear to be a general occurrence. Based on the low number of subjects that experienced SAEs with a causal relationship and the nature, frequency and intensity of observed AEs, the hydromorphone/naloxone groups showed no additional or unexpected risk compared to hydromorphone/placebo treatment. Hence, none of the hydromorphone/naloxone ratio groups gave rise to particular safety concerns.

All ratios (2:1, 1:1, 1:2 and 1:3 ratios) demonstrated a statistically significant improvement in bowel function (BFI score). With respect to the pre-set clinically relevant improvement in bowel function a substantial improvement was observed in the 1:2 and 1:1 ratio groups and a lower improvement was shown by the 1:3 ratio group. Therefore, with respect to the bowel function parameters the 1:1 and 1:2 ratios can be regarded as particularly suited for a fixed combination product.

To obtain further evidence on optimized ratios with respect to BFI, a more detailed analysis of the 1:1 and 1:2 ratio was performed by absolute daily hydromorphone dose with respect to improvement in bowel function, supported by a corresponding analysis on analgesic efficacy. For this purpose a subgroup evaluation was performed analyzing the mean BFI and mean pain values throughout the Double-Blind and Switch-back Phase and also applying the descriptive statistics used for the primary analysis.

The results gathered through the primary analysis of the bowel function, analgesic efficacy and safety parameters, clearly confirmed that the addition of naloxone to the opioid agonist hydromorphone does lead to a clinically relevant improvement of opioid-induced constipation without compromising the analgesic efficacy of hydromorphone or a decreased safety risk, therefore demonstrating a clinical benefit for the pain patients. When adjusting for the naloxone placebo effect the most pronounced clinically relevant improvement was observed for the 1:2 ratio. A clinically relevant improvement in bowel function was also shown in the 1:1 ratio. The 1:3 ratio resulted in a lower clinically relevant improvement in bowel function. This indicates a plateau effect, where the addition of a higher amount of naloxone does not lead to a more distinct improvement of opioid-induced constipation.

Further analysis with respect for BFI values included the additional evaluation, focusing on the comparison of the 1:1 and 1:2 ratios and accounting for the hydromorphone dose. In the 8 mg as well as 24 mg and 48 mg hydromorphone groups the 1:2 showed a markedly clinically relevant improvement in BFI without sacrificing the analgesic efficacy.

The invention inter alia relates to:

1. A solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl: naloxone HCl for use in the treatment of pain in a patient.

2. A solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl: naloxone HCl for use in the treatment of pain and preventing and/or reducing opioid-induced constipation in a patient.

3. A solid oral prolonged release pharmaceutical composition comprising hydromorphone or a pharmaceutically acceptable salt thereof and naloxone or a pharmaceutically acceptable salt thereof in a weight ratio range corresponding to from about 1:1 to about 1:2 of hydromorphone HCl: naloxone HCl for use in the treatment of pain in a patient, wherein the patient experiences opioid-induced constipation as a consequence of treatment with an opioid in the absence of an opioid antagonist.

4. A solid oral prolonged release pharmaceutical composition for use of any of 1, 2, or 3, wherein the administered pharmaceutical composition comprises hydromorphone or a pharmaceutically acceptable salt thereof in an amount corresponding to from and including about 2 mg up to and including about 32 mg of hydromorphone hydrochloride, and naloxone or a pharmaceutically acceptable salt thereof in an amount corresponding to from and including about 2 mg up to and including about 64 mg of naloxone hydrochloride, wherein the prolonged release pharmaceutical composition is suitable for administration every 12 hours.

5. A solid oral prolonged release pharmaceutical composition for use of any of 1, 2, 3, or 4, wherein the administered pharmaceutical composition comprises hydromorphone or a pharmaceutically acceptable salt thereof in an amount corresponding to from and including about 4 mg up to and including about 12 mg of hydromorphone hydrochloride, and naloxone or a pharmaceutically acceptable salt thereof in an amount corresponding to from and including about 4 mg up to and including about 12 mg of naloxone hydrochloride, wherein the pharmaceutical composition comprises hydromorphone or a pharmaceutically acceptable salt thereof and naloxone or a pharmaceutically acceptable salt thereof in a weight ratio corresponding to about 1:1 of hydromorphone HCl:naloxone HCl, and wherein the prolonged release pharmaceutical composition is suitable for administration every 12 hours.

6. A solid oral prolonged release pharmaceutical composition for use of any of 1, 2, 3, or 4, wherein the administered pharmaceutical composition comprises hydromorphone or a pharmaceutically acceptable salt thereof in an amount corresponding to from and including about 4 mg up to and including about 24 mg of hydromorphone hydrochloride, and naloxone or a pharmaceutically acceptable salt thereof in an amount corresponding to from and including about 8 mg up to and including about 48 mg of naloxone hydrochloride, wherein the pharmaceutical composition comprises hydromorphone or a pharmaceutically acceptable salt thereof and naloxone or a pharmaceutically acceptable salt thereof in a weight ratio corresponding to about 1:2 of hydromorphone HCl:naloxone HCl, and wherein the prolonged release pharmaceutical composition is suitable for administration every 12 hours.

7. A solid oral prolonged release pharmaceutical composition for use of any of 1, 2, 3, 4, 5, or 6, wherein the pharmaceutical composition is provided in the form of multiparticulates.

8. A solid oral prolonged release pharmaceutical composition for use of any of 1, 2, 3, 4, 5, 6, or 7, wherein the pharmaceutical composition is provided in the form of multiparticulates, which are mini-tablets.

9. A solid oral prolonged release pharmaceutical composition for use of any of 1, 2, 3, 4, 5, 6, 7, or 8, wherein the pharmaceutical composition is provided in the form of multiparticulates, which are mini-tablets and wherein hydromorphone or a pharmaceutically acceptable salt thereof and naloxone or a pharmaceutically acceptable salt thereof are both embedded in the same matrix particles, on which a prolonged release coating is disposed.

10. A solid oral prolonged release pharmaceutical composition for use of 9, wherein said matrix particles comprising hydromorphone or a pharmaceutically acceptable salt thereof and naloxone or a pharmaceutically acceptable salt thereof in admixture with pharmaceutically acceptable excipients provide for immediate release of hydromorphone or a pharmaceutically acceptable salt thereof and naloxone or a pharmaceutically acceptable salt thereof in the absence of said prolonged release coating.

11. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 64 mg of naloxone hydrochloride.

12. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 64 mg of naloxone hydrochloride.

13. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 64 mg of naloxone hydrochloride, and wherein the patient experiences opioid-induced constipation as a consequence of treatment with an opioid in the absence of an opioid antagonist.

14. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use of any of 11, 12, or 13, wherein hydromorphone or a pharmaceutically acceptable salt thereof is administered in a daily amount corresponding to from and including about 8 mg up to and including about 24 mg of hydromorphone hydrochloride, and naloxone or a pharmaceutically acceptable salt thereof is administered in a daily amount corresponding to from and including about 8 mg up to and including about 24 mg of naloxone hydrochloride.

15. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use of any of 11, 12, 13, or 14, wherein the combination is provided in the form of a solid, oral prolonged release pharmaceutical composition, which is suitable for administration every 12 or 24 hours.

16. A combination of hydromorphone or a pharmaceutically acceptable salt thereof and naloxone or a pharmaceutically acceptable salt thereof in a weight ratio corresponding to about 1:1 of hydromorphone HCl:naloxone HCl for use of any of 11, 12, 13, or 14, wherein hydromorphone or a pharmaceutically acceptable salt thereof is administered every 12 hours in an amount corresponding to from and including about 4 mg up to and including about 12 mg of hydromorphone hydrochloride, and naloxone or a pharmaceutically acceptable salt thereof is administered concomitantly every 12 hours in an amount corresponding to from and including about 4 mg up to and including about 12 mg of naloxone hydrochloride.

17. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride.

18. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride.

19. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 4 mg up to and including about 128 mg of naloxone hydrochloride, and wherein the patient experiences opioid-induced constipation as a consequence of treatment with an opioid in the absence of an opioid antagonist.

20. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use of any of 17, 18, or 19, wherein hydromorphone or a pharmaceutically acceptable salt thereof is administered in a daily amount corresponding to from and including about 8 mg up to and including about 48 mg of hydromorphone hydrochloride, and naloxone or a pharmaceutically acceptable salt thereof is administered in a daily amount corresponding to from and including about 16 mg up to and including about 96 mg of naloxone hydrochloride.

21. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use of any of 17, 18, 19, or 20, wherein the combination is provided in the form of a solid, oral prolonged release pharmaceutical composition, which is suitable for administration every 12 or 24 hours.

22. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use of any of 17, 18, 19, or 20, wherein hydromorphone or a pharmaceutically acceptable salt thereof is administered every 12 hours in an amount corresponding to from and including about 4 mg up to and including about 24 mg of hydromorphone hydrochloride, and naloxone or a pharmaceutically acceptable salt thereof is administered concomitantly every 12 hours in an amount corresponding to from and including about 8 mg up to and including about 48 mg of naloxone hydrochloride.

23. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride.

24. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain and/or reducing opioid-induced constipation in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride.

25. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use in the treatment of pain in a patient, by orally administering hydromorphone or a pharmaceutically acceptable salt thereof in a daily amount corresponding to about 48 mg of hydromorphone hydrochloride, and naloxone or a pharmaceutically acceptable salt thereof in a daily amount corresponding to about 96 mg of naloxone hydrochloride, wherein the patient experiences opioid-induced constipation as a consequence of treatment with an opioid in the absence of an opioid antagonist.

26. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use of any of 23, 24, or 25, wherein the combination is provided in the form of a solid, oral prolonged release pharmaceutical composition, which is suitable for administration every 24 hours.

27. A combination of hydromorphone or a pharmaceutically acceptable salt thereof and naloxone or a pharmaceutically acceptable salt thereof in a weight ratio corresponding to about 1:2 of hydromorphone HCl:naloxone HCl for use of any of 23, 24, or 25, wherein the combination is provided in the form of a solid, oral prolonged release pharmaceutical composition, which is suitable for administration every 12 hours and which comprises 24 mg hydromorphone HCl and 48 mg naloxone HCl.

28. A combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 128 mg of naloxone hydrochloride.

29. A combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use in the treatment of pain and preventing and/or reducing opioid-induced constipation in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 128 mg of naloxone hydrochloride.

30. A combination of hydromorphone or a pharmaceutically acceptable salt thereof and naloxone or a pharmaceutically acceptable salt thereof in a weight ratio corresponding to from about 1:1 to about 1:2 of hydromorphone HCl:naloxone HCl for use in the treatment of pain in a patient, by orally administering hydromorphone or a pharmaceutically acceptable salt thereof in a daily amount corresponding to from and including about 2 mg up to and including about 64 mg of hydromorphone hydrochloride, and naloxone or a pharmaceutically acceptable salt thereof in a daily amount corresponding to from and including about 2 mg up to and including about 128 mg of naloxone hydrochloride, and wherein the patient experiences opioid-induced constipation as a consequence of treatment with an opioid in the absence of an opioid antagonist.

31. A combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use of any of 28, 29, or 30, wherein hydromorphone or a pharmaceutically acceptable salt thereof is administered in a daily amount corresponding to from and including about 8 mg up to and including about 48 mg of hydromorphone hydrochloride, and naloxone or a pharmaceutically acceptable salt thereof is administered in a daily amount corresponding to from and including about 8 mg up to and including about 96 mg of naloxone hydrochloride.

32. A combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use of any of 28, 29, 30, or 31, wherein the combination is provided in the form of a solid, oral prolonged release pharmaceutical composition, which is suitable for administration every 12 or 24 hours.

33. A combination of hydromorphone or a pharmaceutically acceptable salt thereof and naloxone or a pharmaceutically acceptable salt thereof in a weight ratio range corresponding to from about 1:1 to about 1:2 of hydromorphone HCl:naloxone HCl for use of any of 28, 29, 30, or 31, wherein hydromorphone or a pharmaceutically acceptable salt thereof is administered every 12 hours in an amount corresponding to from and including about 4 mg up to and including about 24 mg of hydromorphone hydrochloride, and naloxone or a pharmaceutically acceptable salt thereof is administered concomitantly every 12 hours in an amount corresponding to from and including about 4 mg up to and including about 48 mg of naloxone hydrochloride.

34. A combination of hydromorphone or a pharmaceutically acceptable salt thereof and naloxone or a pharmaceutically acceptable salt thereof for use of any of 11, 12, 13, 14, 15, 16, 27, 18, 19, 20, 21, 22, 23, 24, 25, 26, 27, 28, 29, 30, 31, 32, or 33, wherein the combination is provided as a prolonged release pharmaceutical composition in the form of multiparticulates.

35. A combination of hydromorphone or a pharmaceutically acceptable salt thereof and naloxone or a pharmaceutically acceptable salt thereof for use of any of 11, 12, 13, 14, 15, 16, 27, 18, 19, 20, 21, 22, 23, 24, 25, 26, 27, 28, 29, 30, 31, 32, 33, or 34, wherein the combination is provided as a prolonged release pharmaceutical composition in the form of, which are mini-tablets.

36. A combination of hydromorphone or a pharmaceutically acceptable salt thereof and naloxone or a pharmaceutically acceptable salt thereof for use of any of 11, 12, 13, 14, 15, 16, 27, 18, 19, 20, 21, 22, 23, 24, 25, 26, 27, 28, 29, 30, 31, 32, 33, or 34, wherein the combination is provided as a prolonged release pharmaceutical composition in the form of multiparticulates, which are mini-tablets and wherein hydromorphone or a pharmaceutically acceptable salt thereof and naloxone or a pharmaceutically acceptable salt thereof are both embedded in the same matrix particles, on which a prolonged release coating is disposed.

37. A combination of hydromorphone or a pharmaceutically acceptable salt thereof and naloxone or a pharmaceutically acceptable salt thereof for use of 36, wherein said matrix particles comprising hydromorphone or a pharmaceutically acceptable salt thereof and naloxone or a pharmaceutically acceptable salt thereof in admixture with pharmaceutically acceptable excipients provide for immediate release of hydromorphone or a pharmaceutically acceptable salt thereof and naloxone or a pharmaceutically acceptable salt thereof in the absence of said prolonged release coating.

38. An oral solid prolonged release pharmaceutical composition comprising hydromorphone or a pharmaceutically acceptable salt thereof and naloxone or a pharmaceutically acceptable salt thereof in a weight ratio corresponding to about 1:1 of hydromorphone HCl:naloxone HCl, hydromorphone or a pharmaceutically acceptable salt thereof in amount corresponding to about 12 mg of hydromorphone hydrochloride, and naloxone or a pharmaceutically acceptable salt thereof in an amount corresponding to about 12 mg of naloxone hydrochloride.

39. An oral solid prolonged release pharmaceutical composition comprising hydromorphone or a pharmaceutically acceptable salt thereof and naloxone or a pharmaceutically acceptable salt thereof in a weight ratio corresponding to about 1:2 of hydromorphone HCl:naloxone HCl, hydromorphone or a pharmaceutically acceptable salt thereof in amount corresponding to about 24 mg of hydromorphone hydrochloride, and naloxone or a pharmaceutically acceptable salt thereof in an amount corresponding to about 48 mg of naloxone hydrochloride.

40. An oral solid prolonged release pharmaceutical composition of any of 38 or 39, wherein the pharmaceutical composition is provided in the form of multiparticulates.

41. An oral solid prolonged release pharmaceutical composition of any of 38, 39, or 40, wherein the pharmaceutical composition is provided in the form of multiparticulates, which are mini-tablets.

42. An oral solid prolonged release pharmaceutical composition of any of 38, 39, 40, or 41, wherein the pharmaceutical composition is provided in the form of multiparticulates, which are mini-tablets and wherein hydromorphone or a pharmaceutically acceptable salt thereof and naloxone or a pharmaceutically acceptable salt thereof are both embedded in the same matrix particles, on which a prolonged release coating is disposed.

43. An oral solid prolonged release pharmaceutical composition of 42, wherein said matrix particles comprising hydromorphone or a pharmaceutically acceptable salt thereof and naloxone or a pharmaceutically acceptable salt thereof in admixture with pharmaceutically acceptable excipients provide for immediate release of hydromorphone or a pharmaceutically acceptable salt thereof and naloxone or a pharmaceutically acceptable salt thereof in the absence of said prolonged release coating.

44. An oral solid prolonged release pharmaceutical composition of any of 38, 39, 40, 41, 42, or 43, wherein the pharmaceutical composition is suitable for administration every 12 hours.

45. An oral solid prolonged release pharmaceutical composition of any of 38, 39, 40, 41, 42, 43, or 44 for use in the treatment of pain.

46. An oral solid prolonged release pharmaceutical composition of any of 38, 39, 40, 41, 42, 43, or 44 for use in the treatment of pain and prevention and/or reduction of opioid-induced constipation.

47. An oral solid prolonged release pharmaceutical composition of any of 38, 39, 40, 41, 42, 43, or 44 for use in the treatment of pain in patients, which experience opioid-induced constipation as a consequence of treatment with an opioid in the absence of an opioid antagonist.

The invention claimed is:
1. A method for the treatment of pain in a patient in need thereof, comprising orally administering:
hydromorphone or a pharmaceutically acceptable salt thereof in a daily amount corresponding to about 12 mg to about 64 mg of hydromorphone HCl, and naloxone or a pharmaceutically acceptable salt thereof in a daily amount corresponding to about 24 mg to about 128 mg of naloxone HCl;

wherein the hydromorphone or pharmaceutically acceptable salt thereof and the naloxone or pharmaceutically acceptable salt thereof are administered daily in a weight ratio corresponding to about 1:2 of hydromorphone HCl:naloxone HCl, and wherein the method reduces opioid-induced constipation in the patient.

2. The method of claim 1, wherein the patient has moderate to severe cancer pain.

3. The method of claim 1, wherein the hydromorphone or pharmaceutically acceptable salt thereof and the naloxone or pharmaceutically acceptable salt thereof are provided in the form of a solid, oral prolonged release pharmaceutical composition, which is suitable for administration every 12 or 24 hours.

4. The method of claim 1, wherein the daily amount of the hydromorphone or pharmaceutically acceptable salt thereof corresponds to about 12 mg of hydromorphone HCl, and the daily amount of the naloxone or pharmaceutically acceptable salt thereof corresponds to about 24 mg of naloxone HCl.

5. The method of claim 4, wherein the hydromorphone or pharmaceutically acceptable salt thereof and the naloxone or pharmaceutically acceptable salt thereof are provided in the form of a solid, oral prolonged release pharmaceutical composition.

6. The method of claim 1, wherein the daily amount of the hydromorphone or pharmaceutically acceptable salt thereof corresponds to about 16 mg of hydromorphone HCl, and the daily amount of the naloxone or pharmaceutically acceptable salt thereof corresponds to about 32 mg of naloxone HCl.

7. The method of claim 6, wherein the hydromorphone or pharmaceutically acceptable salt thereof is administered every 12 hours in an amount corresponding to about 8 mg of hydromorphone HCl, and the naloxone or pharmaceutically acceptable salt thereof is administered concomitantly every 12 hours in an amount corresponding to about 16 mg of naloxone HCl.

8. The method of claim 7, wherein the hydromorphone or pharmaceutically acceptable salt thereof and the naloxone or pharmaceutically acceptable salt thereof are provided in the form of a solid, oral prolonged release pharmaceutical composition.

9. A method for the treatment of pain in a patient in need thereof, comprising orally administering:

hydromorphone or a pharmaceutically acceptable salt thereof in a daily amount corresponding to about 24 mg to about 64 mg of hydromorphone HCl, and naloxone or a pharmaceutically acceptable salt thereof in a daily amount corresponding to about 48 mg to about 128 mg of naloxone HCl;

wherein the hydromorphone or pharmaceutically acceptable salt thereof and the naloxone or pharmaceutically acceptable salt thereof are administered daily in a weight ratio corresponding to about 1:2 of hydromorphone HCl:naloxone HCl, and wherein the method reduces opioid-induced constipation in the patient.

10. The method of claim 9, wherein the patient has moderate to severe cancer pain.

11. The method of claim 9, wherein the hydromorphone or pharmaceutically acceptable salt thereof and the naloxone or pharmaceutically acceptable salt thereof are provided in the form of a solid, oral prolonged release pharmaceutical composition, which is suitable for administration every 12 or 24 hours.

12. The method of claim 9, wherein the daily amount of the hydromorphone or pharmaceutically acceptable salt thereof corresponds to about 32 mg of hydromorphone HCl, and the daily amount of the naloxone or pharmaceutically acceptable salt thereof corresponds to about 64 mg of naloxone HCl.

13. The method of claim 12, wherein the hydromorphone or pharmaceutically acceptable salt thereof is administered every 12 hours in an amount corresponding to about 16 mg of hydromorphone HCl, and the naloxone or pharmaceutically acceptable salt thereof is administered concomitantly every 12 hours in an amount corresponding to about 32 mg of naloxone HCl.

14. The method of claim 13, wherein the hydromorphone or pharmaceutically acceptable salt thereof and the naloxone or pharmaceutically acceptable salt thereof are provided in the form of a solid, oral prolonged release pharmaceutical composition.

15. The method of claim 9, wherein the daily amount of the hydromorphone or pharmaceutically acceptable salt thereof corresponds to about 64 mg of hydromorphone HCl, and the daily amount of the naloxone or pharmaceutically acceptable salt thereof corresponds to about 128 mg of naloxone HCl.

16. The method of claim 15, wherein the hydromorphone or pharmaceutically acceptable salt thereof is administered every 12 hours in an amount corresponding to about 32 mg of hydromorphone HCl, and the naloxone or pharmaceutically acceptable salt thereof is administered concomitantly every 12 hours in an amount corresponding to about 64 mg of naloxone HCl.

17. The method of claim 16, wherein the hydromorphone or pharmaceutically acceptable salt thereof and the naloxone or pharmaceutically acceptable salt thereof are provided in the form of a solid, oral prolonged release pharmaceutical composition.

18. The method of claim 9, wherein the hydromorphone or pharmaceutically acceptable salt thereof and the naloxone or pharmaceutically acceptable salt thereof are provided in the form of a solid, oral prolonged release pharmaceutical composition, which is suitable for administration every 12 hours and which comprises:

hydromorphone or pharmaceutically acceptable salt thereof in an amount corresponding to about 12 mg of hydromorphone HCl, and naloxone or pharmaceutically acceptable salt thereof in an amount corresponding to about 24 mg of naloxone HCl.

* * * * *